US007393864B2

(12) United States Patent
Lamb et al.

(10) Patent No.: US 7,393,864 B2
(45) Date of Patent: *Jul. 1, 2008

(54) USE OF CLC3 CHLORIDE CHANNEL BLOCKERS TO MODULATE VASCULAR TONE

(75) Inventors: Fred S. Lamb, Solon, IA (US); Brian C. Schutte, Iowa City, IA (US); Baoli Yang, Cedar Rapids, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 1011 days.

This patent is subject to a terminal disclaimer.

(21) Appl. No.: 09/930,105

(22) Filed: Aug. 15, 2001

(65) Prior Publication Data

US 2002/0065325 A1    May 30, 2002

Related U.S. Application Data

(63) Continuation-in-part of application No. 09/512,926, filed on Feb. 25, 2000, now Pat. No. 7,220,782.

(60) Provisional application No. 60/121,727, filed on Feb. 26, 1999.

(51) Int. Cl.
 A61K 31/445 (2006.01)
 A61K 31/135 (2006.01)
 A61K 31/55 (2006.01)
 A61K 31/40 (2006.01)

(52) U.S. Cl. .................. 514/324; 514/651; 514/212.01; 514/317; 514/428

(58) Field of Classification Search ................ 514/324, 514/651, 212.01, 317, 428
See application file for complete search history.

(56) References Cited

U.S. PATENT DOCUMENTS

| 5,077,601 | A |   | 12/1991 | Hatada et al. ................. 357/81 |
| 5,224,538 | A |   | 7/1993  | Jacoby ....................... 165/166 |
| 5,470,883 | A | * | 11/1995 | Stromberg .................. 514/648 |
| 5,472,985 | A |   | 12/1995 | Grainger et al. ............. 514/651 |
| 5,658,936 | A | * | 8/1997  | Kifor et al. .................. 514/381 |
| 5,691,355 | A |   | 11/1997 | Bryant et al. ................ 514/324 |
| 5,760,066 | A |   | 6/1998  | Tang .......................... 514/378 |
| 5,770,609 | A |   | 6/1998  | Grainger et al. ............. 514/319 |
| 5,795,898 | A |   | 8/1998  | Brown et al. ................ 514/263 |
| 5,811,447 | A |   | 9/1998  | Kunz et al. .................. 514/411 |
| 5,912,805 | A |   | 6/1999  | Freuler et al. ............... 361/705 |
| 5,940,269 | A |   | 8/1999  | Ko et al. ..................... 361/697 |
| 5,957,194 | A |   | 9/1999  | Azar .......................... 165/80.3 |
| 6,015,008 | A |   | 1/2000  | Kogure et al. ............... 165/185 |
| 6,054,198 | A |   | 4/2000  | Bunyan et al. .............. 428/40.5 |
| 6,197,789 | B1|   | 3/2001  | Grainger et al. ............. 514/319 |
| 6,266,560 | B1| * | 7/2001  | Zhang et al. ................. 604/20 |

FOREIGN PATENT DOCUMENTS

WO    WO-96/40098    12/1996

OTHER PUBLICATIONS

Delaney et al. Increased libido: a complication of tamoxifen therapy of male breast cancer. The breast, 1996 5, pp. 53-54.*
Drug Facts and Comparisons, 1997 p. 3162.*
Andreas, S.,et al., "Characterization of cell volume-sensitive chloride currents in freshly prepared and cultured pancreatic acinar cells from early postnatal rats", *J. of Physiology*, 513 (2), (Dec. 1, 1998), 453-465.
Borsani, G.,et al., "Characterization of a Human and Murine Gene (CLCN3) Sharing Similarities to Voltage-Gated Chloride Channels and to a Yeast Integral Membrane Protein", *Genomics*, 27, (1995), pp. 131-141.
Dick, G.M., et al., "Functional and molecular identification of a novel chloride conductance in canine colonic smooth muscle", *Am. J. of Physiology*, 275 (4), Part 1, (Oct. 1998), C940-C950.
Duan, D., et al., "Molecular identification of a volume-regulated chloride channel", *Nature*, 390, (Nov. 1997), pp. 417-421.
Kawasaki, M..,et al .,"Stable and Functional Expression of the ClC-3 Chloride Channel in Somatic Cell Lines", *Neuron*, 14, (Jun. 1995), pp. 1285-1291.
Lamb, F.S., et al., "Chloride ion currents contribute functionally to norepinephrine-induced vascular contraction", *Am. J. Physiol.*, 275, (1998), pp. H151-H160.
Lamb, F.S., et al., "The endothelium modulates the contribution of chloride currents to norepinephrine-induced vascular contraction", *Am. J. Physiol.*, 275, (1998), H161-H168.
Liu, B-X., et al., "Tamoxifen Normalizes the Increase in Vascular Sensitivity Associated with Endothelial Disruption", *FASEB Journal*, 13 (4), Part 1, Abstract, (Mar. 12, 1999), p. A49.
Qiu, X.C., et al., "The cardiovascular reactions mediated by TPA and tamoxifen in spinal cord of conscious rats", *Yaoxue Xuebao*, 30 (7), (1995), 481-485.
Yamazaki, J., et al., "Functional and Molecular expression of volume-regulated chloride channels in canine vascular smooth muscle cells", *J. of Physiology*, 507 (3), (Mar. 15, 1998), 729-736.
Ralph, D. J., et al., "The Treatment of Peyronie's Disease with Tamoxifen", *British Journal of Urology*, 70, Abstract, Database EMBASE on ACS. Accession No. 93001761,(1992),648-651.

* cited by examiner

*Primary Examiner*—Jennifer Kim
(74) *Attorney, Agent, or Firm*—Viksnins, Harris & Padys, PLLP

(57) ABSTRACT

The present invention provides methods for the modulation of vascular tone in a patient having compromised vascular tissue, which methods comprise the administration of a chloride channel blocking agent or a pharmaceutically acceptable salt thereof.

17 Claims, 20 Drawing Sheets

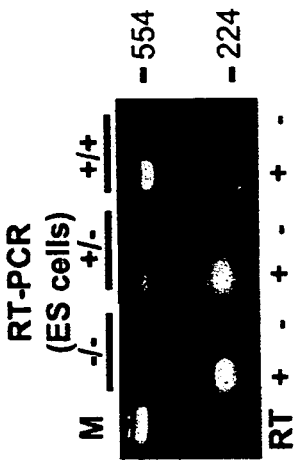
FIG. 4B
FIG. 4C
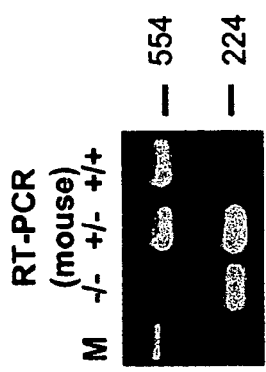
FIG. 4D
FIG. 4E

+/-    -/-    -/-

USE OF CLC3 CHLORIDE CHANNEL BLOCKERS TO MODULATE VASCULAR TONE

CLAIM OF PRIORITY

This application is a continuation-in-part application of U.S. application Ser. No. 09/512,926, filed Feb. 25, 2000, now U.S. Pat. No. 7,220,782 which in turn claims priority under 35 U.S.C. §119(e) from U.S. Provisional Application Serial No. 60/121,727, filed Feb. 26,1999.

STATEMENT OF GOVERNMENT RIGHTS

Portions of the present invention were made with support of the United States Government via grants from the National Institutes of Health (grant numbers NIH HL62483, NIH P30-HD 27748, NIH HL07121, NIH NS02007, and NIH/NIDDK P30DK54759). The U.S. Government therefore may have certain rights in the invention.

BACKGROUND OF THE INVENTION

Male sexual dysfunction, or impotence, may be manifested in various ways: loss of desire, inability to obtain or maintain an erection, premature ejaculation, absence of emission, inability to achieve orgasm. The organic causes of erectile impotence can be grouped into endocrine, drug, local, neurologic, and vascular causes. Vascular insufficiency causes impotence because blood flow into the vascular network of the penis is insufficient to obtain (or maintain) the erect state. Likewise, occlusion in smaller vessels supplying the penis can also lead to impotence. Together with neuropathy, vascular insufficiency contributes to the impotence in many men with diabetes mellitus.

Erectile impotence or dysfunction (ED) may be defined as an inability to achieve or sustain an erection adequate for intercourse. Its prevalence is claimed to be between 2 and 7% of the human male population as a whole, and the incidence increases with age up to 50 years. Between 18 and 75% of the male population between 55 and 80 years of age are impotent. In the U.S.A. alone, for example, it has been estimated that there are up to 10 million impotent males, with the majority suffering from problems of organic rather than psychogenic origin.

Medical therapy with androgens offers little more than placebo benefit except in hypogonadal men. Surgical therapy may be useful in the treatment of decreased potency related to aortic obstruction; however, potency can be lost rather than improved after aortic operation if the autonomic nerve supply to the penis is damaged. A useful surgical technique for improvement of potency in refractory patients such as individuals with diabetic neuropathy is the implantation of a penile prosthesis, e.g., the insertion within the corpora of a small, blunt, SILASTIC® rod. The patient must be made aware that full erection is not produced and that the device only prevents buckling during intercourse. Furthermore, the complication rate is high in some patients. Alternatively, an inflatable prosthetic device has been devised for implantation on either side of the corpora. A connecting reservoir of material is placed in the perivesicular space and pumps are located in the scrotum. By means of these pumps the penis can be made to become nearly fully erect at the appropriate time and to relax after intercourse.

Prostaglandin E-1 (PGE-1; Alprostadil) has been employed successfully in the treatment of erectile dysfunction. Injections of 10 to 60 µg of PGE-1 directly into the corpora cavernosa of the penis have been found to be effective in producing erections sufficient to allow intercourse. The erections are reported to last 30 minutes to one hour, but the dangers associated with self-injection, e.g., infection, trauma, etc. make this treatment method highly undesirable. PGE-1 has also been administered by placing a pellet containing 125 to 1000 µg of the drug into the male urethra using a specially-designed device. This approach, while avoiding the dangers of self-injection, still involves the danger of producing a urethral infection. Other drawbacks include difficulty in adjusting the dose, trauma to the urethra, and vaginal burning in the female partner.

Medical treatment of erectile dysfunction has been attempted using intracavernosal (i.c.) injection of vasoactive substances, and good results have been claimed with phenoxybenzamine, phentolamine, papaverine, and prostaglandin $E_1$, either alone or in combination; however, pain, priapism, and fibrosis of the penis are associated with the i.c. administration of some of these agents. Potassium channel openers (KCO) and vasoactive intestinal polypeptide (VIP) have also been shown to be active i.c., but cost and stability issues could limit development of the latter. An alternative to the i.c. route is the use of glyceryl trinitrate (GTN) patches applied to the penis, which has been shown to be effective but produces side-effects in both patient and partner.

Sublingual administration of apomorphine has been reported to restore normal erectile function through its effect on brain chemistry. However, the response requires 20 to 40 minutes following administration, and apomorphine was found to be effective in returning sexual potency only to about 70% of men whose dysfunction had psychological origins.

The physiologic mechanism of erection of the penis involves the local release of nitric oxide (NO) in the corpus cavernosum during sexual stimulation. NO then activates the enzyme cyclic guanosine monophosphate (cGMP) producing smooth muscle relaxation in the corpus cavernosum and allowing inflow of blood. Sildenafil (VIAGRA®)) is reported to be a selective inhibitor of cyclic-GMP-specific phosphodiesterase type 5 (PDE5), the predominant isozyme metabolizing cyclic GMP formed in the corpus cavernosum. Since sildenafil is a potent inhibitor of PDE5 in the corpus cavernosum, it is believed to enhance the effect of nitric oxide, thereby increasing cavernosal blood flow in the penis, especially with sexual stimulation. Inhibitors of cyclic guanosine 3', 5'-monophosphate phosphodiesterases (cGMP PDEs), such as sildenafil, are useful in the treatment of ED. As disclosed in PCT Publication WO 94/28902, sildenafil compounds may be administered orally, thereby obviating the disadvantages associated with i.c. administration. Inasmuch as sildenafil at the currently recommended doses of 25-100 mg has little effect in the absence of sexual stimulation, sildenafil is believed to restore the natural erectile response to sexual stimulation but not cause erections in the absence of such stimulation. See, for example, Goldstein et al., *The New England Journal of Medicine*, 338, 1397-1404 (1998). The localized mechanism by which cGMP stimulates relaxation of the smooth muscles has not been elucidated.

In dose-response studies, increasing doses of sildenafil (25 to 100 mg) reportedly increased the erectogenic efficacy of sildenafil. However, the time to onset of action of periorally administered drugs is long and highly variable, due to differences in absorption based on a wide variety of factors, from the size and age of the patient to the interval since, and size and composition of, the last meal consumed by the patient. However, the oral administration of sildenafil is also accompanied by dose-responsive undesirable side effects. At dosages higher than 50 milligrams, the incidence of such side effects as abnormal vision problems ranging from blue or green halo effects to blurring, dyspepsia, nasal congestion, blinding headaches, flushing redness, diarrhea, dizziness, rash, and urinary tract infection increases. Other more serious side effects have been reported, such as syncope (loss of consciousness), priapism (erection lasting 4 hours or more) and increased cardiac risk (coital coronaries), can be brought on in some cases by physiological predisposition, adverse drug interaction or potentiation, or by drug abuse.

In addition, consistent with its known effects on the NO/cGMP pathway, sildenafil has been shown to potentiate the hypotensive effects of nitrates. Hypotension crisis can result from the combination of sildenafil citrate and organic nitrates, causing, in some cases death, so its administration to patients who are concurrently using organic nitrates (such as nitroglycerin) in any form is contraindicated. Moreover, the long-term effects of large doses of sildenafil containing drugs is not known. See, for example, Handy B., *Time,* 50-57 (May 4, 1998).

In a healthy vasculature, vascular smooth muscle (VSM) is covered by a monolayer of endothelial cells (FIG. 1). Healthy VSM contracts in response to vasoconstrictor agonists, including norepinephrine (NE). Lamb and Barna, *Am. J. Physiol.,* 275, H151 (1998). Disruption of the endothelial layer has been shown to increase sensitivity to these agonists. These findings are consistent with studies which showed that changes in the basal production of NO alters VSM responsiveness to vasoconstrictors. Joulow-Schaeffer et al., *Am. J. Physiol.,* 259, R38 (1990); Rees et al., *Proc. Natl. Acad. Sci. USA,* 86, 3375 (1989); Wiklund et al., *Eur. J. Pharmacol.,* 185, 123 (1990). Medical procedures, such as balloon angioplasty, or disease-induced or genetically-influenced pathologies, such as diabetes and hypertension, create the risk or predisposition for compromised vascular tissue, i.e., damage to the endothelial cell monolayer. In addition, endothelial damage in itself may exacerbate these pathologic processes and contribute to symptoms which are associated with them. For instance, coronary artery disease results in localized endothelial damage, and sudden surges in natural vasoconstrictors (such as NE) can cause heart failure. Previous treatments for these endothelially compromised patients have been limited to chemicals agents which cause system-wide VSM relaxation, and consequently, frequently cause side effects such as orthostasis (dizziness) due to transient low blood pressure during certain activities.

Chloride ion channels are present in VSM (Klockner, *Pflugers Arch.,* 424 231 (1991); Lamb et al., *Circ. Res.,* 75 742 (1994)) and have been shown to be activated by vasoconstrictor agonists (Klockner and Isenberg, *Pflugers Arch.,* 418, 168 (1991); Pacaud et al., *Br. J. Pharmacol.,* 97 139 (1989)). Chloride ion currents have also been shown to contribute functionally to norepinephrine-induced contraction of normal vasculature. Lamb and Barna, *Am. J. Physiol.,* 275 H151 (1998). In that study, tamoxifen was shown to have no effect on the norepinephrine-induced contraction of normal vasculature (vasculature with intact endothelium). In Lamb and Barna, *Am. J. Physiol.,* 275, H161 (1998), the endothelium was shown to modulate the contribution of the chloride currents to norepinephrine-induced VSM constriction. The effects of tamoxifen on endothelium-compromised tissue was not studied, since no effect was seen in normal tissues. In other studies, a particular chloride ion channel, "CLC3", was shown to be responsible for swelling-induced chloride conductance. Duan et al., *Nature* 390, 417 (1997). Tamoxifen was shown to block the ion channel responsible for swelling-induced chloride conductance, a result which had previously been demonstrated. Nilius et al., 428 Pflugers Arch 364 (1994).

The effects of tamoxifen on estrogen levels, and concomitant effects on other systems, including NE and dopamine expression, have also been studied. Kocsis et al., *Br J Exp Path,* 157 (1988); Etgen and Petitti, *J Neurochem,* 49, 1732 (1987); Baksi et al., *Neuropharm,* 20, 1163 (1981). Moreover, a method for treating peripheral vasoconstriction with tamoxifen citrate has been disclosed in U.S. Pat. No. 5,470,883. In that patent, the anti-estrogen effects of tamoxifen were said to be responsible for reducing the peripheral vasoconstriction of exogenously-administered adrenergic compound.

There exists a need for a method of treating a patient with compromised vascular tissue, e.g., an endothelially-compromised patient, a patient having erectile dysfunction.

SUMMARY OF THE INVENTION

In general, the present invention provides methods to reduce the sensitivity of endothelially-compromised vascular smooth muscle. In certain embodiments, methods are herein provided to influence blood pressure, in a tissue-selective manner, by administering a chloride channel ClC3 ("ClC3") blocker. In contrast to previous agents which cause patients to have system-wide vascular smooth muscle relaxation, it is now possible to affect only the pathologic vascular smooth muscle. In other words, use of ClC3 blockers allows for tissue-targeting in a highly specific and reliable manner, which results in avoidance of the unpleasant side effects of system-wide vasodilation associated with previously-known treatments.

The present invention provides methods to reduce the sensitivity of endothelially compromised vascular smooth muscle in a patient in need of such reduction, comprising administering a pharmaceutically effective amount of a ClC3 blocker. In particular, methods are provided to reduce the sensitivity of endothelially-compromised vascular smooth muscle, comprising administering a compound of Formula I.

Preferred are methods to reduce the sensitivity of endothelially-compromised vascular smooth muscle, comprising administering a compound of Formula I

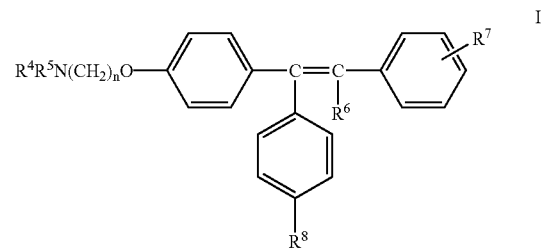

wherein
either $R^4$ is H or a lower alkyl radical and $R^5$ is a lower alkyl radical, or $R^4$ and $R^5$ are joined together with the adjacent nitrogen atom to form a heterocyclic radical; $R^6$ is H or a lower alkyl radical; $R^7$ is H, halo, OH, a lower alkyl radical, or is a buta-1,3-dienyl radical which together with the adjacent benzene ring forms a naphthyl radical;
$R^8$ is H or OH; and
n is 2;

or a pharmaceutically acceptable salt thereof.

In particular, the compound administered is 1-p-β-dimethylaminoethoxyphenyl-trans-1,2-diphenylbut-1-ene (tamoxifen), or a pharmaceutically acceptable salt thereof. Tamoxifen has the chemical structure:

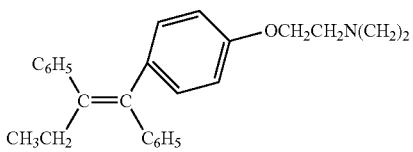

Also provided are methods to ameliorate the negative effects associated with vascular smooth muscle endothelium damage in a patient is need of such treatment, comprising administering a pharmaceutically-effective amount of a ClC3 blocker, or a pharmaceutically acceptable salt thereof. In particular are methods as described comprising administering a pharmaceutically effective amount of a compound of Formula I

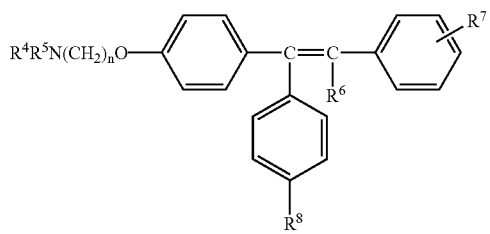

wherein wherein either $R^4$, $R^5$, $R^6$, $R^7$, and $R^8$ are defined as hereinabove and n is 2; or a pharmaceutically acceptable salt thereof.

In addition, methods as provided wherein said endothelium damage is the result of diabetes, surgical procedure, coronary artery disease or hypertension.

Methods which further comprise administering a pharmaceutically-effective compound such as an anti-hypertension agent, an anti-diabetes agent, and anti-coronary artery disease agent, an anti-restenosis agent, and vasodilatory agent are also provided.

There are also provided methods to affect ClC3 receptors comprising administering a compound of Formula I

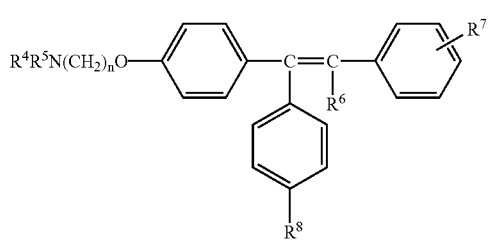

wherein either $R^4$, $R^5$, $R^6$, $R^7$, and $R^8$ are defined as hereinabove and n is 2; or a pharmaceutically acceptable salt thereof. In particular, the compound administered is 1-p-β-dimethylaminoethoxyphenyl-trans-1,2-diphenylbut-1-ene (tamoxifen), or a pharmaceutically acceptable salt thereof.

Additionally, there are provided methods to reduce contraction of endothelially-compromised vascular smooth muscle in response to a vasoconstrictive agent, comprising administering a ClC3 blocker, or a salt thereof, for example, a compound of Formula I

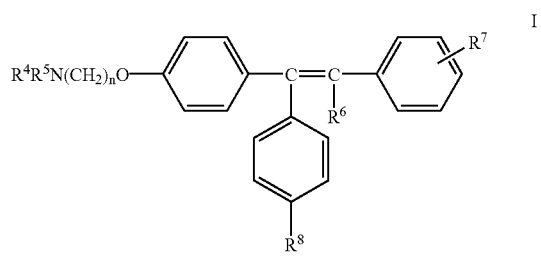

wherein either $R^4$, $R^5$, $R^6$, $R^7$, and $R^8$ are defined as hereinabove and n is 2; or a pharmaceutically acceptable salt thereof. In particular, the compound administered is 1-p-β-dimethylaminoethoxyphenyl-trans-1,2-diphenylbut-1-ene (tamoxifen), or a pharmaceutically acceptable salt thereof. In addition, methods are provided as described, wherein the agonist is, in particular, norepinephrine (NE).

Also provided are methods to decrease the effects of vasoconstrictors in pathologic tissues and not in non-pathologic tissues in a patient with pathologic tissues, and who is in need of such decrease, comprising administering a pharmaceutically-effective amount of a ClC3 blocker, or a pharmaceutically acceptable salt thereof. For example, methods are provided as described wherein the ClC3 blocker is a compound of Formula I

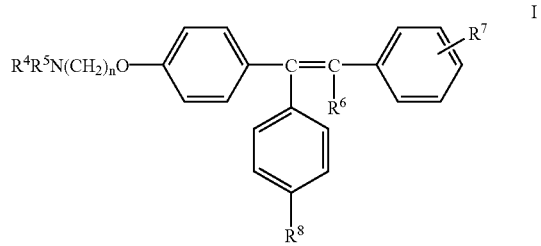

wherein either $R^4$, $R^5$, $R^6$, $R^7$, and $R^8$ are defined as hereinabove and n is 2; or a pharmaceutically acceptable salt thereof. Moreover, methods are provided as described wherein the compound administered is in particular 1-p-β-dimethylaminoethoxyphenyl-trans-1,2-diphenylbut-1-ene (tamoxifen), or a pharmaceutically acceptable salt thereof.

Also provided herein are methods to stabilize blood pressure in patients with endothelium-compromised vascular smooth muscle, and who are in need of such stabilization, comprising administering a pharmaceutically effective amount of a ClC3 blocker. In particular, the ClC3 blocker is a compound of Formula I

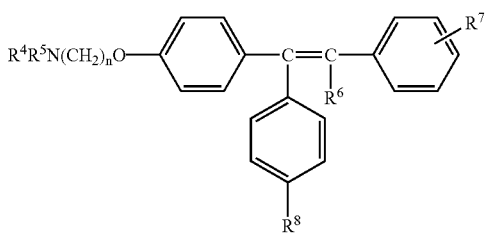

wherein either $R^4$, $R^5$, $R^6$, $R^7$, and $R^8$ are defined as hereinabove and n is 2; or a pharmaceutically acceptable salt thereof. In particular, the compound administered is 1-p-β-dimethylaminoethoxyphenyl-trans-1,2-diphenylbut-1-ene (tamoxifen), or a pharmaceutically acceptable salt thereof.

The present invention also provides methods to modulate the vascular tone, e.g., enhance vasodilation, of compromised vascular tissue, e.g., vascular tissue associated with diabetes, a surgical procedure, hypertension, coronary artery disease or erectile dysfunction, by the administration of a chloride channel blocking agent. In certain embodiments, methods are herein provided to modulate vascular tone in a tissue-selective manner, by administering a ClC3 blocker.

Thus, the present invention provides a method to modulate vascular tone in a patient having compromised vascular tissue, which method involves administering a pharmaceutically effective amount of a chloride channel blocking agent, or a pharmaceutically acceptable salt thereof. A chloride channel blocking agent of the invention can be a compound of Formula I

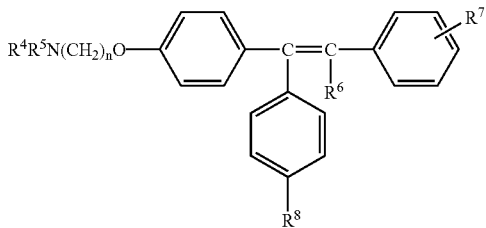

wherein either $R^4$, $R^5$, $R^6$, $R^7$, and $R^8$ are defined as hereinabove and n is 2; or a pharmaceutically acceptable salt thereof. In particular, the compound can be 1-p-β-dimethylaminoethoxyphenyl-trans-1,2-diphenylbut-1-ene (tamoxifen), or a pharmaceutically acceptable salt thereof.

Alternatively, the chloride channel blocking agent can be niflumic acid, mefanamic acid, flufenamic acid, or a stilbene disulphonate, such as 4,4'-diisothiocyanostilbene-2,2'-disulphonic acid (DIDS), 4,4'-dinitrostilbene-2,2'-disulphonic acid (DNDS), and 4-acetamido-4'isiothiocyanostilbene-2,2'-disulphonic acid (SITS); anthracene-9-carboxylic acid (9-AC), 5-Nitro-2-(3-phenylpropylamino)benzoic acid (NPPB), diphenylamine-2-carboxylate (DPC), indanyloxyacetic acid-94 (IAA-94), or the pharmaceutically acceptable salts thereof. In particular, the agent can be DIDS or a pharmaceutically acceptable salt thereof.

An agent of the invention can be administered systemically, e.g., orally or intravenously. Additional pharmaceutically effective compounds may also be administered, such as an anti-diabetes agent; an anti-hypertension agent, an anti-coronary artery disease agent, an anti-restenosis agent, and a vasodilatory agent.

A particular chloride channel of the invention is ClC3. In a particular method of the invention, blocking the CLC3 channel can result in diminished vasoconstriction to norepinephrine. In another particular method of the invention, the chloride channel blocking agent modulates vascular tone by enhancing vasodilation.

Also provided is a method to modulate penile vascular tone in a mammal which involves administering a pharmaceutically effective amount of a chloride channel blocking agent, or a pharmaceutically acceptable salt thereof. For example, the chloride channel blocker is a compound of Formula I:

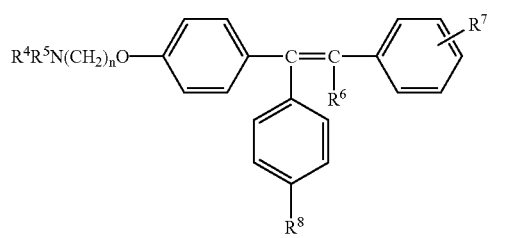

wherein either $R^4$, $R^5$, $R^6$, $R^7$, and $R^8$ are defined as hereinabove and n is 2; or a pharmaceutically acceptable salt thereof. In particular, the compound can be tamoxifen or a pharmaceutically acceptable salt thereof. Alternatively, the agent can be niflumic acid, mefanamic acid, flufenamic acid, a stilbene disulphonate, for example, 4,4'-diisothiocyanostilbene-2,2'-disulphonic acid (DIDS), 4,4'-dinitrostilbene-2,2'-disulphonic acid (DNDS), or 4-acetamido-4'isiothiocyanostilbene-2,2'-disulphonic acid (SITS); anthracene-9-carboxylic acid (9-AC), 5-Nitro-2-(3-phenylpropylamino) benzoic acid (NPPB), diphenylamine-2-carboxylate (DPC), indanyloxyacetic acid-94 (IAA-94), or any of the pharmaceutically acceptable salts thereof. In particular, the agent can be DIDS or a pharmaceutically acceptable salt thereof, and the agent can be administered orally or intravenously.

In particular, the chloride channel can be a CLC3 channel, and blocking the CLC3 channel results in diminished vasoconstriction to norepinephrine, and/or a reduction in penile sympathetic tone, which can induce an erection.

Further provided is a method for treating male impotence, which method involves administering a composition having a CLC3 channel blocking agent or a pharmaceutically acceptable salt thereof, and a pharmaceutically acceptable carrier.

DETAILED DESCRIPTION OF THE INVENTION

I. Definitions

Figure 1:
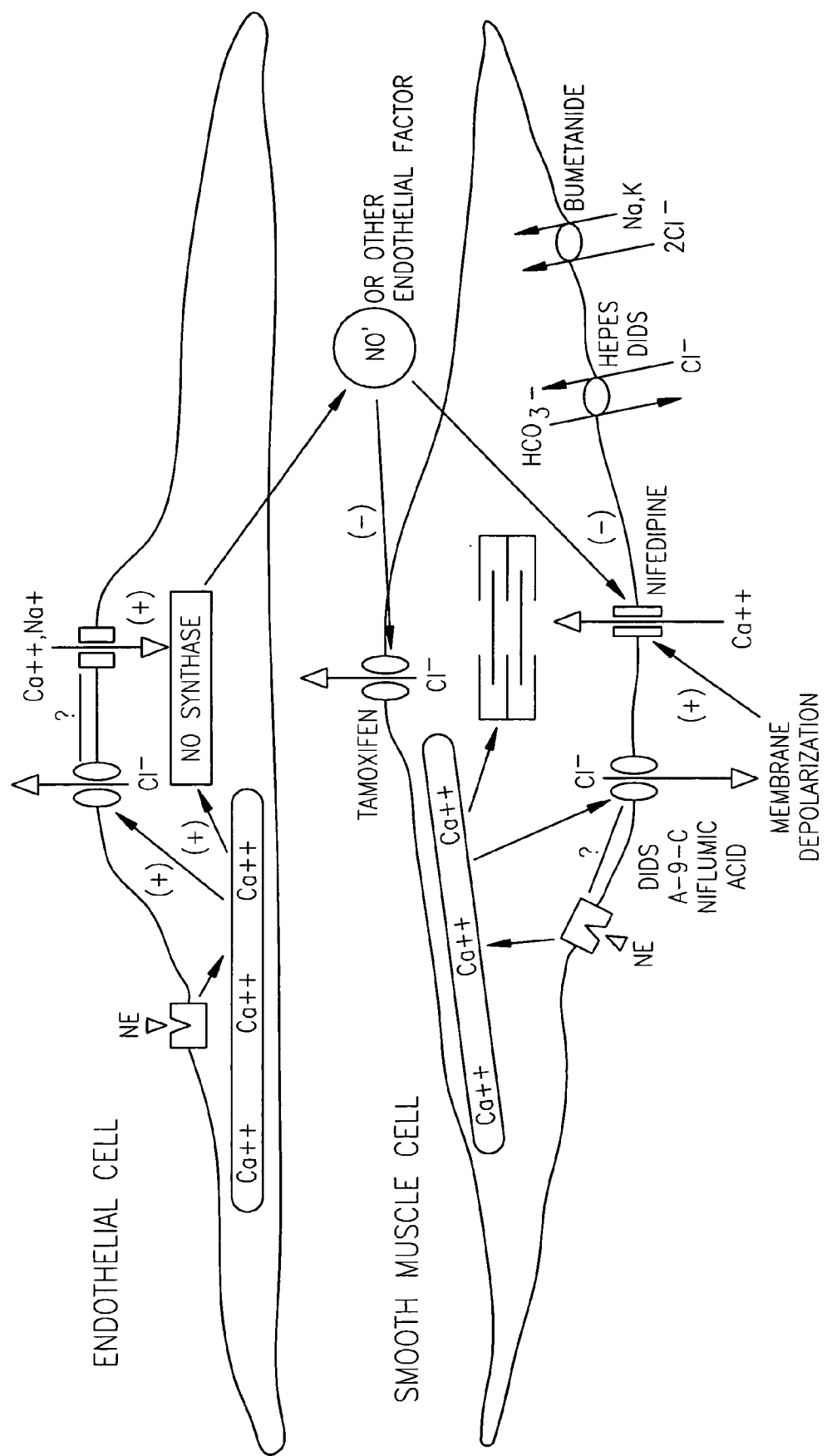
FIG. 1: is a diagram of normal blood vessel surface layers.

As used herein, "agent" refers to any compound or composition made by any means, including synthetic or naturally-occurring compounds or compositions, whether purified or not, and can include: herbal extract (s); precursor (s); metabolite (s); and ingredient (s), including enantiomer (s) of a racemic mixture. The definition of "agent" includes any compound or composition as described in this paragraph that has been shown to be active for the desired medical purpose, including any agent which works to affect a desired medical result, and/or is approved by the U.S. Food & Drug Administration, or foreign equivalent.

An "anti-coronary artery disease agent" means any agent which causes reduction in the effects of coronary artery disease, and/or which is considered by the medical or scientific community, or the general public, to reduce coronary artery disease or the symptoms associated with coronary artery disease.

An "anti-diabetes agent" means any agent which causes reduction in diabetes, and/or which is considered by the medical or scientific community, or the general public, to reduce diabetes or the symptoms associated with diabetes.

An "anti-hypertension agent" means any agent which causes reduction in hypertension, and/or which is considered by the medical or scientific community, or the general public, to reduce hypertension or the symptoms associated with hypertension.

An "anti-restenosis agent" means any agent which causes reduction in restenosis, and/or which is considered by the medical or scientific community, or the general public, to reduce restenosis or the symptoms associated with restenosis.

A "vasodilatory agent" means any agent which causes dilation of blood vessels, i.e., widening of the lumen of blood vessels, and/or which is considered by the medical or scientific community, or the general public, to diminish, e.g., reduce, vasoconstriction.

By "CLC" or "ClC" is meant a chloride ion channel. The CLC family has nine known members in mammals that show a differential tissue distribution and function both in plasma membranes and in intracellular organelles. CLC proteins have about 10-12 transmembrane domains, and have been reported to function as dimers and may have two pores. In particular, "CLC3" or "ClC3" refers to chloride ion channel 3, and has the same meaning as CLC-3 or ClC-3.

The term "chloride channel blocker" or "chloride channel blocking agent" refers to an agent that directly or indirectly inhibits chloride channel conductance, such as an anion transport inhibitor, e.g., a Cl$^-$ transport inhibitor, or an anion channel blocker. In particular, a "CLC3 blocker" is an agent that inhibits or blocks the conductance of a CLC3 channel.

By "compromised vascular tissue" is meant vascular tissue that is mechanically compromised, e.g., by a medical procedure, such as balloon angioplasty, which results in damage or disruption to the endothelial cell monolayer associated with smooth muscle cells, or that is compromised by a disease-induced, genetically-influenced or other vascular disorder, such as diabetes, hypertension, vascular insufficiency or neuropathy, that either creates the risk or predisposition for damage to the endothelial cell monolayer associated with smooth muscle cells or results in an abnormal, i.e., unhealthy, vasculature.

By "damage" is meant any reduction in physiological or structural function, whether caused by mechanical, chemical or other means. The standard for determining whether function is "reduced" is determined by comparing the state of being in question to either population normals or individual normals. Moreover, if CLC3 blockers, in particular, tamoxifen or tamoxifen analogues are able to decrease vascular sensitivity to agonists in the patient, "damage" is assumed.

"Surgical procedure" means any medical procedure requiring mechanical or mechanical/chemical manipulation of a patient's body, wherein said procedure results in damage to the endothelium layer adjoining vascular smooth muscle.

By "enhance" is meant activate, improve, increase, or induce.

An "effective amount" means that dosage of active compound (s) sufficient to provide therapeutic treatment of the specified medical indication.

A "patient" means any living organism with vascular smooth muscle, such as a mammal, and, in particular, a human.

II. Chloride Channel Blocking Agents of the Invention

A chloride channel blocking agent of the invention is Formula I, the descriptive chemical terms of which have their usual meaning. For example, the term "halo" includes bromo, chloro, fluoro, and iodo. The term "lower alkyl" or "$C_1$-$C_4$ alkyl" refers to the straight and branched aliphatic radicals of 1-4 carbon atoms including methyl, ethyl, propyl, isopropyl, n-butyl, isobutyl, sec-butyl, and tert-butyl. In addition, the term "substituted phenyl" refers to a phenyl molecule having one or two substituents selected from the group consisting of $C_1$-$C_4$ alkyl, $C_1$-$C_5$ alkoxy, hydroxy, nitro, chloro, fluoro, or tri (chloro or fluoro) methyl. Finally, the term "$C_1$-$C_4$ alkoxy" includes the straight and branched aliphatic ether radicals of 1-4 carbon atoms such as methoxy, ethoxy, propoxy, isopropoxy, n-butoxy, isobutoxy, sec-butoxy, and tert-butoxy.

In particular, a compound of the invention is a compound of Formula I, in which $R^4$ and $R^5$ each are methyl, $R^6$ is ethyl, $R^7$ and $R^8$ each are H, and n is 2, is known in the art as tamoxifen. Tamoxifen and its analogs are most well known as antiestrogen compounds and tamoxifen primarily is used for the treatment of breast carcinoma in women. See, *The Merck Index*, 11th Ed., 1430 (1989).

Tamoxifen citrate (Nolvadex. RTM., Zeneca Pharmaceuticals, Wilmington, Del. 19897) is a trans-isomer of a triphenylethylene derivative. Tamoxifen citrate has a molecular weight of 563.62, the pKa is 8.85, the equilibrium solubility in water at 37° C. is 0.5 mg/mL, and in 0.002N HCI at 37° C., it is 0.2 mg/mL.

In addition to tamoxifen, a chloride channel blocking agent of the invention includes niflumic acid; mefanamic acid; flufenamic acid; a stilbene disulphonate, e.g., 4,4'-diisothiocyanatostilbene-2,2'-disulphonic acid (DIDS), 4,4'-dinitrostilbene-2,2'-disulphonic acid (DNDS), and 4-acetamido-4'isiothiocyanatostilbene-2,2'-disulphonic acid (SITS); anthracene-9-carboxylic acid (9-AC); 5-Nitro-2-(3-phenyl-propylamino)benzoic acid (NPPB); diphenylamine-2-carboxylate (DPC); indanyloxyacetic acid-94 (IAA-94); or a pharmaceutically acceptable salt thereof. In particular, a chloride channel blocking agent of the invention is DIDS or a pharmaceutically acceptable salt thereof.

III. Dosages, Formulations and Routes of Administration of the ClC3 Blocking Agents of the Invention The CLC3 blocking agents of the invention, and the pharmaceutically acceptable salts thereof, are preferably administered in therapeutically effective, vasodilatory amount. To achieve this effect(s), the ClC3 blocking agents, e.g., 4,4'-diisothiocyanato stilbene-2,2'-disulphonic acid (DIDS), SITS, niflumic acid, or pharmaceutically effective salt thereof, may be administered at dosages of at least about 0.001 to about 100 mg/kg, more preferably about 0.01 to about 10 mg/kg, and even more preferably about 0.1 to about 1 mg/kg, of body weight, although other dosages may provide beneficial results. For example, DIDS may be administered to a patient in a dose range between about 20 mg/day to about 80 mg/day. The amount administered will vary depending on various factors including, but not limited to, the agent(s) chosen, the weight, the physical condition, and the age of the mammal, and whether prevention or treatment is to be achieved. Such factors can be readily determined by the clinician employing animal models or other test systems which are well known to the art.

Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

A CLC3 blocking agent, e.g., tamoxifen, may be administered alone, with other vasodilatory agents that are known to the art.

Thus, one or more suitable unit dosage forms comprising the therapeutic agents of the invention, which, as discussed below, may optionally be formulated for sustained release. For example, the unit dosage forms of the invention may be formulated using microencapsulation, see WO 94/07529, and U.S. Pat. No. 4,962,091 the disclosures of which are incorporated by reference herein. Materials for microencapsulation include, for example, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers. Preferred carriers are polysaccharides such as hyaluronic acid, sodium alginate and dextran sulfate. More preferably, a therapeutic agent of the invention is encapsulated in alginate beads. See, for example, U.S. Pat. No. 5,879,712.

Alginates also have been used in fluid suspensions for many years because of their ability to form a gel upon contact with gastric fluids. Alginate is a collective term for a family of copolymers containing 1,4-linked-D-mannuronic and -L-guluronic acid residues in varying proportions and sequential arrangement. Alginate forms gels with divalent ions like calcium, and the gel-forming properties are strongly correlated with the proportion and lengths of the blocks of contiguous L-guluronic acid residues in the polymeric chains. Preferred sustained release dosage forms comprise a CLC3 blocking agent of the invention, e.g., tamoxifen encapsulated in alginate beads (see, for example, Joki et al., Nat. Biotech., 19, 35 (2001)).

Thus, the unit dosage forms comprising the therapeutic agents of the invention can be administered by a variety of routes including oral, or parenteral, including by rectal, transdermal, subcutaneous, intravenous, intramuscular, intraperitoneal, intrathoracic, intrapulmonary and intranasal (respiratory) routes. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for oral administration, they are preferably combined with a pharmaceutically acceptable carrier, diluent or excipient to form a pharmaceutical formulation, or unit dosage form. Preferably, orally administered therapeutic agents of the invention are formulated for sustained release, e.g., the agents are microencapsulated. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Pharmaceutical formulations containing the therapeutic agents of the invention can be prepared by procedures known in the art using well-known and readily available ingredients. For example, the agent can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing the agents of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing an agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets of an agent of the invention are designed to resist disintegration in the stomach and dissolve in the more neutral to alkaline environment of the duodenum.

The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$-$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and alpha-tocopherol and its derivatives may be mentioned. The galenical forms chiefly conditioned for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap.

Additionally, the agents are well suited to formulation as sustained release dosage forms and the like. The formulations can be so constituted that they release the active ingredient only or preferably in a particular part of the intestinal or respiratory tract, possibly over a period of time. The coatings, envelopes, and protective matrices may be made, for example, from polymeric substances, such as polylactideglycolates, liposomes, microemulsions, microparticles, nanoparticles or waxes. These coatings, envelopes, and protective matrices are useful to coat indwelling devices, e.g., stents, catheters, peritoneal dialysis tubing, and the like. Preferably, the peptides are formulated as microspheres or nanospheres.

The therapeutic agents of the invention can be delivered via patches for transdermal administration. See U.S. Pat. No. 5,560,922 for examples of patches suitable for transdermal delivery of a therapeutic agent. Patches for transdermal delivery can comprise a backing layer and a polymer matrix which has dispersed or dissolved therein a therapeutic agent, along with one or more skin permeation enhancers. The backing layer can be made of any suitable material which is impermeable to the therapeutic agent. The backing layer serves as a protective cover for the matrix layer and provides also a support function. The backing can be formed so that it is essentially the same size layer as the polymer matrix or it can be of larger dimension so that it can extend beyond the side of the polymer matrix or overlay the side or sides of the polymer matrix and then can extend outwardly in a manner that the surface of the extension of the backing layer can be the base for an adhesive means. Alternatively, the polymer matrix can contain, or be formulated of, an adhesive polymer, such as polyacrylate or acrylate/vinyl acetate copolymer. For long-term applications it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness will be from about 10 to about 200 microns.

Generally, those polymers used to form the biologically acceptable adhesive polymer layer are those capable of forming shaped bodies, thin walls or coatings through which therapeutic agents can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix by skin moisture would affect the release rate of the therapeutic agents as well as the capability of the dosage unit to remain in place for convenience of removal.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydrogel), polyvinylidene chloride, poly(ethylene terephthalate), butyl rubber, epichlorohydrin rubbers, ethylenvinyl alcohol copolymers, ethylene-vinyloxyethanol copolymers; silicone copolymers, for example, polysiloxane-polycarbonate copolymers, polysiloxane polyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoroethylene; and the like.

Preferably, a biologically acceptable adhesive polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after dispersing the therapeutic agent into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

Preferably, a plasticizer and/or humectant is dispersed within the adhesive polymer matrix. Water-soluble polyols are generally suitable for this purpose. Incorporation of a humectant in the formulation allows the dosage unit to absorb moisture on the surface of skin which in turn helps to reduce skin irritation and to prevent the adhesive polymer layer of the delivery system from failing.

Therapeutic agents released from a transdermal delivery system must be capable of penetrating each layer of skin. In order to increase the rate of permeation of a therapeutic agent, a transdermal drug delivery system must be able in particular to increase the permeability of the outermost layer of skin, the stratum corneum, which provides the most resistance to the penetration of molecules. The fabrication of patches for transdermal delivery of therapeutic agents is well known to the art.

For topical administration, the therapeutic agents may be formulated as is known in the art for direct application to a target area. Conventional forms for this purpose include wound dressings, coated bandages or other polymer coverings, ointments, creams, lotions, pastes, jellies, sprays, and aerosols. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or U.S. Pat. No. 4,051,842. The percent by weight of a therapeutic agent of the invention present in a topical formulation will depend on various factors, but generally will be from 0.01% to 95% of the total weight of the formulation, and typically 0.1-25% by weight.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The agent may be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of a specific indication or disease. Any statistically significant attenuation of one or more symptoms of an indication or disease that has been treated pursuant to the method of the present invention is considered to be a treatment of such indication or disease within the scope of the invention.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0. saline solutions and water.

The agents of the present invention can be administered as a dry powder or in an aqueous solution. Preferred aerosol pharmaceutical formulations may comprise, for example, a physiologically acceptable buffered saline solution containing between about 0.1 mg/ml and about 100 mg/ml of one or more of the agents of the present invention specific for the indication or disease to be treated.

Dry aerosol in the form of finely divided solid peptide or nucleic acid particles that are not dissolved or suspended in a liquid are also useful in the practice of the present invention. Peptide or nucleic acid may be in the form of dusting powders and comprise finely divided particles having an average particle size of between about 1 and 5 m, preferably between 2 and 3 m. Finely divided particles may be prepared by pulverization and screen filtration using techniques well known in the art. The particles may be administered by inhaling a predetermined quantity of the finely divided material, which can be in the form of a powder.

For administration to the upper (nasal) or lower respiratory tract by inhalation, the therapeutic agents of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator, or a metered-dose inhaler (see, for example, the pressurized metered dose inhaler (MDI) and the dry powder inhaler disclosed in Newman, S. P. in Aerosols and the Lung, Clarke, S. W. and Davia, D. eds., pp. 197-224, Butterworths, London, England, 1984).

Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.).

For intra-nasal administration, the therapeutic agent may be administered via nose drops, a liquid spray, such as via a plastic bottle atomizer or metered-dose inhaler. Typical of atomizers are the Mistometer (Wintrop) and the Medihaler (Riker).

In particular, an agent of the invention can be administered systemically, e.g., orally or intravenously.

The formulations and compositions described herein may also contain other ingredients such as antimicrobial agents, or preservatives. Furthermore, the active ingredients may also be used in combination with other therapeutic agents, for example, bronchodilators.

Preferred delivery systems for a peptide can include coupling the peptide to a carrier or an intact attenuated microbe, such as an inactivated virus or attenuated bacterium, e.g., weakened Salmonella, preparing a multiple antigen peptide, using liposomes or other immunostimulating complexes. Preferably, the delivery system enhances the immunogenicity of the peptide. Preferred carrier proteins include large antigenic proteins such as DTD and TTD, or a fusion protein having a carrier protein of bacterial, e.g., Salmonella flagellin, or viral origin. Viral vectors that may be employed to deliver nucleic acid encoding the peptide include, but are not limited to, retroviral vectors, vaccinia virus vectors, adenovirus vectors or canarypox virus vectors.

Compounds of the present invention, can be formulated alone or in combination with another pharmaceutical agent, and can generally will be administered in a convenient formulation. The following formulation examples only are illustrative and are not intended to limit the scope of the present invention.

| Ingredient | Quantity (mg/capsule) |
|---|---|
| Formulation 1: Gelatin Capsules | |
| Hard gelatin capsules are prepared using the following: | |
| Formula I compound | 0.1-1000 |
| Starch, NF | 0-650 |
| Starch flowable powder | 0-650 |
| Silicone fluid 350 centistokes | 0-15 |
| Formulation 2: Formula I capsule | |
| Formula I compound | 1 |
| Starch, NF | 112 |

| Ingredient | Quantity (mg/capsule) |
|---|---|
| Starch flowable powder | 225.3 |
| Silicone fluid 350 centistokes | 1.7 |
| Formulation 3: Formula I capsule | |
| Formula I compound | 5 |
| Starch, NF | 108 |
| Starch flowable powder | 225.3 |
| Silicone fluid 350 centistokes | 1.7 |
| Formulation 4: Formula I capsule | |
| Formula I compound | 10 |
| Starch, NF | 103 |
| Starch flowable powder | 225.3 |
| Silicone fluid 350 centistokes | 1.7 |
| Formulation 5: Formula I capsule | |
| Formula I compound | 50 |
| Starch, NF | 150 |
| Starch flowable powder | 397 |
| Silicone fluid 350 centistokes | 3.0 |

The specific formulations above may be changed in compliance with the reasonable variations provided, and can include other pharmaceutically-active agents, such as those used to treat hypertension, diabetes, coronary artery disease and restenosis.

A tablet formulation is prepared using the ingredients below:

| Ingredient | Quantity (mg/tablet) |
|---|---|
| Formulation 6: Tablets | |
| Formula I compound | 2.5-1000 |
| Cellulose, microcrystalline | 200-650 |
| Silicon dioxide, fumed | 10-650 |
| Stearate acid | 5-15 |

The components are blended and compressed to form tablets.

Alternatively, tablets each containing 25-1000 mg of a formula I compound are made up as follows:

| Formulation 7: Tablets | |
|---|---|
| Ingredient | Quantity (mg/tablet) |
| Formula I compound | 25-1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The Formula I compound, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 500°-60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 25-1000 mg of medicament per 5 ml dose are made as follows:

Formulation 8: Suspensions

| Ingredient | Quantity (mg/5 ml) |
|---|---|
| Sodium carboxymethyl cellulose | 50 mg |
| Syrup | 1.25 mg |
| Benzoic acid solution | 0.10 mL |
| Flavor | q.v. |
| Color | q.v. |
| Purified water | to 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Diagnosis of hypertension, diabetes, restenosis, coronary artery disease or other endothelium-compromised vascular smooth muscle states is within skill of the art, and is evidenced by the internal medicine textbook, such as Harrison's.

Determination whether a compound is a CLC3 blocker can be accomplished according to the Examples herein described.

The compounds can be purchased from commercial sources, such as Sigma Chemical, St. Louis, Mo. However, one skilled in the art is aware how to synthesize these compounds de novo using conventional methods. In particular, compounds of Formula I can be prepared according to the procedures described in U.S. Pat. No. 4,623,600, which patent is hereby incorporated by reference. Pharmaceutically acid addition salts can be prepared according to the disclosure in U.S. Pat. No. 5,691,355, which patent is hereby incorporated by reference.

The invention will be described with reference to the following non-limiting examples.

EXAMPLES

In studies by the present inventors, it was discovered that DIDS (4,4'-diisothiocyanato stilbene-2,2'disulphonic acid) and niflumic acid significantly inhibited the contractile response to ED80 concentrations of norepinephrine (NE) or potassium chloride (KCl) in isolated rings of rat aorta with an intact endothelium. Significantly, tamoxifen did not alter these responses. These vasodilator effects of DIDS and niflumic acid (in the presence of NE or KCl) were endothelium-independent because they persisted in epithelium-denuded blood vessel segments. The effect of tamoxifen on denuded blood vessel segments was not studied, since no effect was apparent in intact vessels. The above experiments were reported in Lamb and Barna, *Am. J. Physiol.*, 275 H151 (1998) and Lamb and Barna, *Am. J. Physiol.*, 275, 161 (1998), and are incorporated herein by reference.

Example 1

Assay Materials and Methods

Adult male Sprague-Dawley rats (250-300 g) were obtained from Harlan Sprague Dawley. The animals were killed by exposure to 100% $CO_2$ for 5 minutes, followed by cervical dislocation. Thoracic aortas were removed, cleaned of adherent connective tissue, and cut into 6 mm rings. The endothelium was left intact, and the rings were mounted in individual 10 ml isolated organ chambers using standard methods for recording of isometric tension. Contractile responses were recorded with an eight-channel MacLab8E and stored on a Power Macintosh 7200 computer. Passive stretch was set at 2.5 g, and the rings were allowed to equilibrate in physiological salt solution (PSS) at 37° C. for 120 minutes before the start of experimentation. PSS was aerated with a mixture of 95% 2-5% $CO_2$; the composition was as follows (in mM): 130 NaCl, 4.7 KCl, 1.18 $KH_2PO_4$, 1.17 $MgSO_4 7H_2O$, 14.9 $NaHCO_3$, 1.6 $CaCl_2H_2O$, 5.5 dextrose, and 0.03 $CaNa_2$-EDTA 0.03 (pH 7.30).

The blood vessel segments were pretreated, for 30 minutes, either with a 1:1000 dilution of ethanol, or with 10 μM tamoxifen (in ethanol, from Sigma Chemical, St. Louis, Mo.).

Sensitivity was quantified by measuring the 50% effective dose of agonist ($ED_{50}$) by linear regression following log transformation of the agonist concentration and logit transformation of the response data. Data were expressed as a percentage of the maximal response of each ring to the agonist.

Example 2

Tamoxifen Normalizes NE Induced VSM Sensitivity

Figure 2:
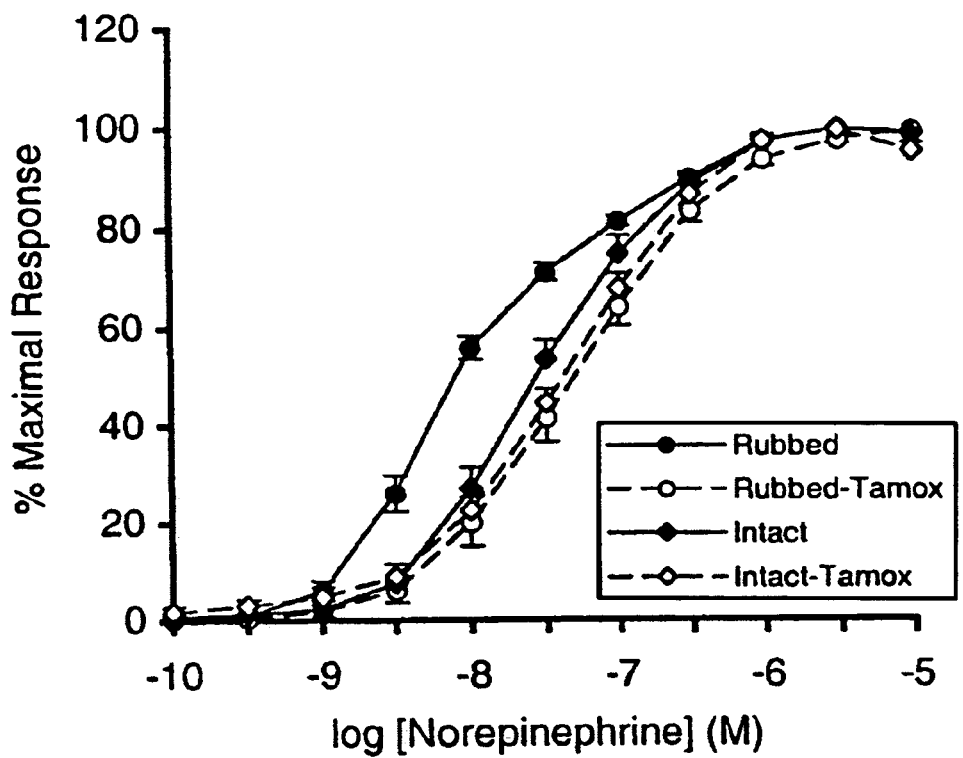
FIG. 2 shows that tamoxifen shifts the dose-response curve of NE back to the right in endothelially compromised vascular smooth muscle, and normalizes the contractile responses, so that there is no longer a significant difference in sensitivity between intact and compromised vessels.

1. Intact and denuded aortic blood vessel segments were prepared, mounted as described in Example 1.
2. Blood vessel segments were pretreated with tamoxifen was measured as described in Example 1. Control blood vessel segments were pretreated with ethanol at the same concentration used to dissolve the tamoxifen.
3. Aliquots of NE (Sigma Chemical, St. Louis, Mo.), which had been dissolved directly into aqueous solution was applied to the vessel segments at concentrations between $10^{-10}$ and $10^{-5}$ M, and the contractile response measured as described above. The results are shown in FIG. 2. In general, the results show that tamoxifen treated denuded blood vessel segments were similar in contractility to intact blood vessels, whereas denuded blood vessel segments which were not treated with tamoxifen were more sensitive to NE than intact blood vessels. The $ED_{50}$ values calculated for NE were as follows: Denuded blood vessel segments=$1.55 \pm 0.19 \times 10^{-8}$ M (control), $5.85 \pm 1.51 \times 10^{-8}$ M (tamoxifen, $p<0.05$); Intact blood vessel segments=$3.41 \pm 0.72 \times 10^{-8}$ M (control), $3.28 \pm 0.41 \times 10^{-8}$ M (tamoxifen).

Example 3

Tamoxifen Normalizes KCl Induced VSM Sensitivity

Figure 3:
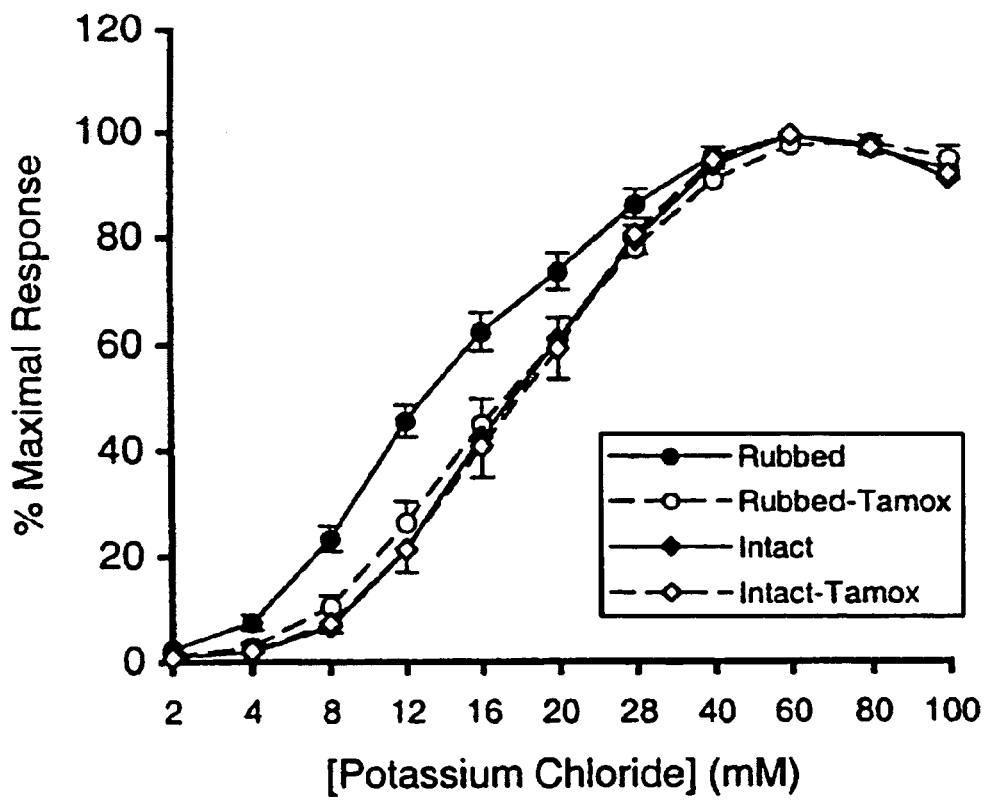
FIG. 3 shows that tamoxifen treatment corrects the increase in vascular smooth muscle sensitivity to KCl associated with mechanical removal of the endothelium.

1. Intact and denuded aortic blood vessel segments were prepared and mounted as described in Example 1.
2. Test blood vessel segments were pretreated with tamoxifen as described in Example 1. Control blood vessel segments were pretreated with ethanol at the same concentration used to dissolve the tamoxifen.
3. Cl (Sigma Chemical, St. Louis, Mo.), was applied to the vessels at 2, 4, 8, 12, 16, 20, 28, 40, 60, 80, and 100 mM concentrations, and the contractile response measured as described above. The results are shown in FIG. 3.

In general, the results show that tamoxifen-treated denuded blood vessel segments were similar in contractility to intact blood vessels, whereas denuded blood vessel segments which were not treated with tamoxifen were more sensitive to KCl than intact blood vessels. The $ED_{50}$ values calculated for KCl were as follows: Denuded blood vessel segments=12.3±0.70 mM (control), 16.9±1.4 mM (tamoxifen, p<0.05); Intact blood vessel segments=17.6±1.6 mM (control), 17.5±1.6 mM (tamoxifen).

Example 4

Estrogen Receptors not Responsible for Tamoxifen Normalization of Agonist Sensitivity Electrophysiology. Chloride ion currents were measured from cultured human aortic and coronary vascular smooth muscle cells at room temperature (22-24° C. using standard whole-cell voltage-clamp techniques (Hamill et al., 1981; Lamb et al., 1994) and an Axopatch 200B patch-clamp amplifier driven by pClamp software (Axon Instruments). The hypotonic (250 mOsm/kg by freezing point depression) bath solution contained (mM): NaCl 125, $MgCl_2$ 2.5, $CaCl_2$ 2.5, HEPES 10, pH 7.2. Isotonic bath solution had the same ionic composition as the hypotonic solution except that the osmolality was adjusted to 300 mOsm/kg by adding mannitol. Pipette solution contained (mM): N'-methyl-D-glucamine chloride (NMDG—Cl) 135, EGTA 2, Mg-ATP 5, HEPES 10, pH 7.2 with osmolality adjusted to 300 mOsm/kg by adding mannitol. Thus, the chloride equilibrium potential remained 0 mV under both isotonic and hypotonic conditions. All components of the buffer solutions were obtained from Sigma. Pipette resistances were 3-5 MOhms.

Patch-clamp recording of the swelling-induced Cl ion current from cultured vascular smooth muscle cells revealed that this current is inhibited by tamoxifen, using methods described above. In contrast, β-estradiol (E, $10^{-7}$ M) did not inhibit but rather increased the swelling-induced Cl current (ICl, pA) seen under hypotonic conditions at +120 mV (hypotonic only=1451±495 pA, hypotonic plus estradiol=3513±856, n=5). This result suggests that the ability of Tamoxifen to inhibit this current cannot be accounted for by tamoxifen-induced activation of estrogen receptors.

Example 5

Protein Kinase C Inhibition not Responsible for Tamoxifen Normalization of Agonist Sensitivity The methods as described in Example 4 were used in this example as well. The protein kinase C (PKC) inhibitor H-7 ($10^{-5}$ M) increased the swelling-induced chloride current above the level induced by hypotonic buffer alone. However, tamoxifen still inhibited the swelling-induced current in the presence of H-7 (hypotonic=1204±313 pA, hypotonic +H7+ tamoxifen=878±493 pA, n=3). This result suggests that activation of PKC is not the mechanism by which tamoxifen inhibits the swelling-induced chloride current.

Example 6

Clcn3 CHLORIDE CHANNEL DEFICIENT MICE

The voltage-gated chloride ion channel ClC-3, encoded by the murine Clcn3 gene, is widely expressed at the tissue level and highly conserved through evolution. It has been proposed by various groups to be either an exclusively intracellular channel involved in regulation of vesicle acidification, or a plasmalemmal conductance that is activated by calcium-calmodulin-dependent protein kinase II, or the ubiquitous swelling-induced chloride conductance ($ICl_{swell}$). A mouse lacking the Clcn3 gene was created, and no loss of $ICl_{swell}$ in cultured vascular smooth muscle cells from $Clcn3^{-/-}$ mice was found. These animals are small and die suddenly with a 10-month mortality of 60%. Additional abnormalities include kyphosis, priapism, absence of hindlimb escape extension upon tail elevation, and as is disclosed elsewhere, altered vascular reactivity (Dickerson et al., 2001). $Clcn3^{-/-}$ mice also display a central nervous system phenotype marked by postnatal degeneration of the hippocampus and of retinal photoreceptors resulting in blindness. A characteristic spatiotemporal pattern of hippocampal degeneration beginning in the dentate gyrus and progressing sequentially to involve CA3 and CA1 pyramidal cells is described herein. Hippocampal degeneration is also region-dependent, beginning anteriorly and progressing posteriorly, with relative sparing of posterior hippocampus. Despite this brain abnormality, $Clcn3^{-/-}$ mice (4-5 weeks old) were remarkably resistant to pentylenetetrazole-induced seizures compared to homozygous wild type or heterozygous controls. Heterozygous mice exhibited no differences from wild type mice in any characteristic or parameter evaluated. Disruption of the Clcn3 gene results in a wide range of abnormalities that are not limited to the central nervous system.

ClC-3 is a member of the ClC family of voltage-gated chloride ion channels (Jentsch et al, 1999). ClC proteins share a common structural pattern with intracellular N- and C-termini, 12 membrane spanning domains, and mature ClC ion channels probably exist as dimers (Fahlke et al., 1997 and Ludewig et al., 1996). ClC-3 was first cloned by Kawasaki and coworkers (Kawasaki et al., 1994) and shown to be highly expressed in rat brain. Subsequently, the homologous human (CLCN3) and murine (Clcn3) genes were identified and found to differ from each other by only 2 amino acid residues out of 760 (Borsani et al., 1995). This high degree of sequence conservation suggests that ClC-3 may serve a role of fundamental importance throughout evolution.

The functional significance of several other members of the ClC family have been made apparent by mutations resulting in inherited human diseases. The functions of other members have been elucidated by characterization of gene-targeted mice. ClC-1 is the predominant anion conductance in skeletal muscle. Mutations in CLCN 1, which encodes ClC-1, cause congenital myotonia due to impaired repolarization causing a defect in muscle relaxation (Klocke et al., 1994 and Kock et al., 1992). Mice lacking the ClC-2 channel undergo degeneration of the retina and testes, leading to blindness and male infertility. This abnormality may be related to disruption of cells responsible for maintaining the blood-retina and blood-testes barriers (Bosl et al., 2001). Mice and humans lacking ClC-7 channels develop osteopetrosis. This failure of bone resorption results when ClC-7 fails to regulate acidification of the resorption lacunae formed by osteoclasts (Kornak et al., 2001).

At least three CLC channels are involved in renal function. ClC-K proteins are expressed mainly in kidney (Kieferle et al., 1994), reside in the plasma membrane (Uchida et al., 2000) and form constitutively open chloride channels (Waldegger et al., 2000). Deletion of the gene for ClC-K1 leads to nephrogenic diabetes insipidus in mice (Uchida et al., 2000). In humans, mutations of the CLCNKB gene cause Bartters syndrome type III, which involves substantial salt loss from the distal tubule and the ascending limb of Henle's loop. This finding suggests that ClC-Kb mediates basolateral chloride efflux (Simon et al., 1997). ClC-3 belongs to the branch of the ClC family that also contains ClC-4 and ClC-5. In humans, mutations in CLCN5 cause Dent's disease, which involves impaired endocytosis and a defect in renal salt transport that results in proteinuria and hypercalciuria. In turn, these abnormalities lead to kidney stones, renal calcification, and kidney failure (Lloyd et al., 1996 and Piwon et al., 2000). Mice lacking Clcn4 displayed no obvious phenotype (Palmer et al., 1995).

To date, efforts to define the function of ClC-3 have generated more controversy than firm conclusions. When ClC-3 was initially expressed in Xenopus oocytes and Chinese hamster ovary cells, the cells produced outwardly rectifying currents that did not inactivate at positive potentials and were blocked by activation of protein kinase C (PKC) (Kawasaki et al., 1994). Subsequently, it was proposed that ClC-3 is the ubiquitous, swelling-induced Cl conductance. Expression of ClC-3 in NIH/3T3 fibroblasts yielded large, swelling-activated, outwardly rectifying and steeply inactivating currents that were inhibited by PKC-dependent phosphorylation. Mutations in the putative pore-forming region of ClC-3 resulted in altered ion selectivity of the swelling-induced current (Duan et al., 1997). Mutations in a consensus PKC phosphorylation site in the intracellular amino terminus of the ClC-3 channel protein appeared to alter the volume-sensing function of the channel (Duan et al., 1999). Antisense oligonucleotides inhibited ClC-3 protein expression in bovine ciliary epithelial cells, decreased the volume-activated chloride current and delayed the activation of the current (Wang et al., 2000). Most recently, the swelling-activated Cl current was blocked in several cell types by an anti-ClC-3 antibody (Duan et al., 2001).

In contrast, some investigators have either been unable to obtain functional expression of ClC-3 currents (Friedrich et al., 1999) or have seen currents that were not regulated by changes in cell volume (Shimada et al, 2000 and Huang et al., 2001). Very recently, Stobrawa and colleagues reported the presence of normal swelling-activated currents in hepatocytes and pancreatic acinar cells derived from Clcn3$^{-/-}$ mice and argue that ClC-3 is predominantly an intracellular anion channel located in vesicle membranes and regulates acidification of synaptic vesicles (Stobrawa, 2001). This argument derives support from the fact that the yeast ClC, GEF1, regulates acidification of post-golgi vesicles (Schwappach et al., 1998) and the GEF1 mutant phenotype can be complemented by a ClC-3 homolog (Miyazaki et al., 1999). In contrast, other investigators have observed plasmalemmal expression of ClC-3 in hepatocytes (Li et al., 2000). Most recently, epithelial cells stably transfected with the full-length human CLCN3 gene demonstrate calcium-calmodulin dependent protein kinase II (CaMKII) regulation of the plasma membrane expression of human ClC-3 channels (Huang et al., 2001). In those experiments, when constitutively active CaMKII was dialyzed into cells expressing ClC-3, membrane chloride current density increased by 22-fold. This effect of CaMKII was abolished by a specific peptide inhibitor of the enzyme. ClC-3 expression did not alter the swelling-induced chloride current. Clearly, significant debate remains regarding the true nature of the ClC-3 current.

Independently, a mouse and an embryonic stem cell (ES) line lacking the Clcn3 gene were created. These data were presented in preliminary form (Schutte et al., 2000). The Clcn3$^{-/-}$ mice display a central nervous system (CNS) phenotype similar to that observed by Stobrawa et al. (Stobrawa, 2001) including progressive postnatal loss of hippocampal neurons and rapid degeneration of retinal photoreceptors. Additional abnormalities include kyphosis, priapism, unexplained premature sudden death, absence of normal escape extension upon tail elevation and, as we report elsewhere, altered vascular reactivity (Dickerson et al., 2001). There is no loss of the swelling-induced Cl current in cultured vascular smooth muscle cells that lack the Clcn3 gene. Because of the early onset and severe photoreceptor degeneration seen in this mouse model, we assessed a cohort of 173 human patients with severe photoreceptor degenerations for mutations in the human homolog of the Clcn3 gene. No etiologic mutations were observed in this population.

Methods

Construction of Replacement Vector and Gene Targeting

A Clcn3 replacement vector, pBYClc3, was constructed in two cloning steps. For the 3' homology, a 3.6 kb Bgl II fragment, including part of intron 7, exons 8 and 9, and part of intron 9, was subcloned into the BamHI site of pOSdupdel (a gift of O. Smithies, University of North Carolina at Chapel Hill). The BclI site located within intron 7 was removed by digestion with BclI and Klenow filling-in. For the 5' homology, a 2.1 kb PCR fragment, containing part of intron 5 and part of exon 6, was subcloned into the BclI and XhoI sites of pOSdupdel. This targeting vector deletes part of the transmembrane domain 2, located in exon 6, and all of transmembrane 3 and 4, located in exon 7. The targeting construct was linearized and introduced into R1 embryonic (ES) cells (129X1/SvJ×129S1/Sv) via electroporation. The ES cells were then cultured for 24 hours in regular medium (DMEM-H+15% FCS) and 10 to 14 days in selection medium (regular medium+G418 at 200 µg/ml+Gancyclovir at 2 µM). Surviving colonies were picked and expanded for screening. The colonies were analyzed by Southern blot analysis using NdeI restriction digestion and hybridization with a 1 kb PCR product amplified from intron 9. Of the 69 colonies picked, two showed the distinct targeted allele and were used for generation of chimeras via blastocyst microinjection.

Generation of Clcn3$^{-/-}$ Mice.

The parental ES cell line R1 was derived from mouse strain 129/SvJ, which carries an Agouti (A$^W$) coat color marker. ES cells heterozygous for the mutant Clcn3 alleles were injected into C57B1/6J blastocysts. Chimeric animals were bred and the DNA of their progeny assayed for the presence of the mutant allele. Both lines (derived from the two colonies isolated above) of chimeras transmitted the ES genome to the next generation when chimeric males were bred to C57B1/6J females. Heterozygous F1 hybrids were intercrossed to generate homozygotes. Thus, the genetic background of the animals used in this study is a mixture of 129/Sv and C57B1/6J.

Progeny were genotyped using PCR. Primers specific for the wild type allele were derived from exon 7 and intron 7 (forward, 5'TACATGTTGCCTGCTGCTGT-3'; (SEQ ID NO:1); reverse, 5'-CTGCAGCACTCAACTCCAGA-3'(SEQ ID NO:2)) and primers specific for the knockout allele were derived from the neomycin gene (forward, 5'-TGAATGAACTGCAGGACGAG-3'(SEQ ID NO:3); reverse, 5'-ATACTTTCTCGGCAGGAGCA-3'(SEQ ID NO:4)). The mouse genotype was further verified by reverse transcription (RT) PCR using a forward primer from exon 5 (5'AGTGGAAAACATGGGCAGAG-3'(SEQ ID NO:5)) coupled with a reverse primer from exon 8 (5'-ACGGCTGTTACCAAATGGAT-3'(SEQ ID NO:6)). These primers amplify a 554 bp product from the wild-type allele and a 224 bp product from the knockout allele.

Reverse Transcription and PCR

Total RNA was purified from mouse brain using the recommended procedure for the RNA/DNA Kit (Qiagen, Valencia, Calif.). The cDNA was generated from 0.5 µg RNA with M-MLV Reverse Transcriptase (Life Technologies, Gibco BRL) and oligo dT primers in the recommended buffer. The PCR reactions contained 1 µl of cDNA or 40 ng of total mouse DNA along with 0.25 U BIO-X-ACT DNA polymerase (Bioline, Kenilworth, N.J.) in the recommended buffer with 1.5 mM $MgCl_2$, 200 µM dNTPs, and 1 µM primers. The conditions for the PCR experiments were 94° denaturation for 2 minutes, 57° annealing for 30 seconds, 68° extension for 1 minute, 35 cycles.

Preparation of Cultured $Clcn3^{-/-}$ Embryonic Stem Cells

In order to make homozygous $Clcn3^{-/-}$ ES cells, one of the two targeted ES cell lines (heterozygous) was cultured in an elevated G418 concentration (1.6 mg/ml) for one week. We did not find a single clone with both alleles altered from more than 200 clones. A new targeting vector with a different selectable marker (hygromycin) was made. A PCR fragment containing the coding region of hygromycin and SV40 promoter was amplified from the plasmid pIND/Hygro (Invitrogen, Carlsbad, Calif.) using the following primers: Clc3Hygf: 5' GGG CCT CGA GGA ATG TGT GTC AGT TAG GGT GTG G 3'(SEQ ID NO:7), Clc3Hygr: 5' GGC CGA TTA ATT AAT GCA GCT GGC ACG ACA GG 3'(SEQ ID NO:8). A XhoI site was introduced to the forward primer and Pac I was introduced to the reverse primer (underlined). The Neo cassette was removed from pBYClc3 with XhoI and PacI digestion and the PCR fragment containing the Hyg cassette was inserted to form pBYClc6.

Electroporation was performed as above except $Clcn3^{+/-}$ ES cells were used and the ES cells were selected under three drugs: hygromycin (150 µg/ml), G418 and Gancyclovir. ES cells were genotyped by RT-PCR as described above. Two positive clones were found of 500 clones screened. ES cells used for RT-PCR analyses were initially grown on top of feeder cells. ES cell colonies were picked into culture dishes with feeder layer and cells were cultured in the presence of Leukemia Inhibitory Factor (1,000 U/ml) in regular medium. The ES cells were separated from the feeder cells prior to genotyping as follows. ES cells were trypsinized in the original plate and let sit for 20 min at 37° C. Feeder cells are larger and therefore sank to the bottom of the plate faster than ES cells, and began to attach to the plate by the end of the incubation period. ES cells were then transferred to a gelatinized plate. This procedure was repeated once more to ensure that no feeder cells remained.

Preparation of Cultured Vascular Smooth Muscle Cells

Primary tissue explants were made from young adult knockout and wild type mouse aortae using established methods (Freshney, 2000). The tissues were minced and washed three times in Dulbecco's phosphate buffered saline (PBS) (Gibco). These explants were seeded into a cell culture flask in DMEM medium (Gibco), 15% FBS, 1% Penn/Strep, 1% Fungizone and incubated at 37° C. and 5% $CO_2$. Once vascular smooth muscle cells had grown to surround the explanted tissue, these cells were transferred into a new flask and the cells were allowing to grow to near confluency. Cells for patch clamp recording were then subcultured at low density onto 9 mm glass disks. The genotype of each line of cultured cells was reconfirmed by PCR.

Mouse Husbandry

All mice were fed standard mouse chow and water, ad libitum, and maintained on a 12:12 light:dark schedule. Care of the mice in these experiments met or exceeded the standards set forth by the National Institutes of Health in their guidelines for the care and use of experimental animals. All procedures were approved by the University Animal Care and Use Committee at the University of Iowa.

Phenotyping: Growth, Survival, General Appearance, Behavior

Mice were weighed at the time of tail tissue collection for genotyping, at weaning and periodically thereafter. The mouse colony was checked for animal deaths daily and fully inventoried at least once each month in order to assess survival of the different groups of mice. The escape extension response to tail elevation was evaluated by measuring the time to onset of rear-leg folding in unsedated mice held by the tail, 1 foot above a flat surface for 1 minute.

To quantify spinal kyphosis, mice were sedated with midazolam HCl, (10 g/kg s.c, Roche) and suspended by the tail in front of an X-ray film cassette for both lateral and frontal position X-rays of skeletal structure. The force applied to straighten the spine therefore consisted of the body weight of each individual mouse. This sedated, suspension method controlled for variations in muscle tone and avoided artifactual curvatures associated with positioning of an unconscious mouse. Thoraco-lumbar and cervico-thoracic angles were measured with a protractor from lateral view X-rays. Knockouts were gender-matched to heterozygote littermates, and when an appropriate littermate was not available, an age and gender-matched control was used.

Electroretinograms (ERGs) were recorded using commercially available equipment (LKC Technologies, Gaithersburg, Md.). Animals were dark-adapted overnight and bright flash ERGs were recorded using a Ganzfeld stimulator at an intensity of 0.6 $cds/m^2$. The mice were anesthetized with a mixture of ketamine (150 mg/kg) and xylazine (7 mg/kg). Pupils were dilated with 1% cyclopentolate hydrochloride and 2.5% phenylephrine hydrochloride. ERGs were recorded utilizing a Burian-Allen corneal electrode (Hansen Laboratories, Iowa City, Iowa) with a reference electrode in the mouth and a subcutaneous ground electrode.

Histology

For neuropathological studies, wild type, heterozygous and knockout mice were sacrificed at a series of postnatal ages. These ages included postnatal day (PD) 24, PD75 (2.5 months), PD165 (5.5 months), PD270 (9 months) and PD330 (11 months). Three animals of each genotype were included at each time point. Following a lethal injection of pentobarbital (>50 mg/kg, i.p., to effect), the mice were perfused via the left ventricle with ice cold 0.9% saline, followed by a fixative containing 4% paraformaldehyde in 0.1 M phosphate buffer. The brains were removed and stored in cold fixative for a minimum of 1 week. Next, some of the brains were dehydrated through a graded series of alcohol, prior to paraffin embedment. The paraffin-embedded tissue was cut on a rotary microtome in the coronal plane at a thickness of 6 micrometers. Sections throughout the rostral-caudal axis of the brain were mounted onto glass slides and stained with cresyl violet. The remaining fixed brains were placed into 30% sucrose in 0.1 M sodium phosphate until they sank. Forty-micrometer-thick frozen sections were cut horizontally on a sliding microtome. A 1:4 series of sections were mounted onto glass slides and were Nissl-stained with cresyl violet. All samples were examined by light microscopy.

To determine whether the neuronal loss observed in the knockout mice was accompanied by astrogliosis, a separate set of sections from the same animals were stained immunohistochemically for glial fibrillary acidic protein (GFAP), a specific marker for astrocytes within the CNS. These sections were first incubated with 3% hydrogen peroxide for 30 minutes, followed by goat serum blocking solution for 60 minutes, then incubated with a monoclonal guinea pig anti-mouse GFAP antibody (Sigma, St. Louis, Mo.). Detection was performed using biotinylated goat anti-guinea pig secondary antibody (Vector Laboratories, Burlingame, Calif.), followed by ABC Elite (Vector) and diaminobenzidine (Vector). PBS was used for all dilutions and rinses.

For studies of eye and somatic histology, tissues were obtained from deeply anesthetized animals perfused retrogradely via the abdominal aorta with PBS followed by 4% paraformaldehyde as above. Tissues were dissected and examined at the macroscopic level before additional fixation in 4% paraformaldehyde in PBS. Fixed tissue was embedded in paraffin, sectioned (8 μm), stained by hematoxylin and eosin (H&E) according to standard protocols and examined by light microscopy. Additional tissues for confirmatory purposes were dissected immediately upon sacrifice of unperfused animals and post-fixed in 4% paraformaldehyde for at least 2 weeks.

Drug Tests for Seizure Susceptibility

The proconvulsant, pentylenetetrazole (PTZ), was dissolved at 7 mg/ml in sterile 0.9% NaCl and administered to drug-naive mice at 70 mg/kg i.p. in a quiet daytime laboratory setting. Parameters measured during the 15-minute observation period included time to onset of generalized tonic-clonic or tonic seizures, and duration of the first generalized seizure. Lethality was assessed 60 minutes post-injection (Loscher and Nolting, 1991).

Blood Tests

Blood gasses were measured using an IL 1620 blood gas analyzer (Instrumentation Laboratories, Lexington, Mass.) on mixed venous retro-orbital blood samples drawn with capillary tubes from sedated mice (midazolam HCl, Roche, 10 mg/kg s.c). Hematocrits were measured from separate retro-orbital blood samples in 70 μg capillary tubes that were permitted to stand vertically for one hour before being spun (5 min) in a capillary microcentrifuge. Osmolality was measured on serum samples with a #5004 Micro Osmometer (Precision Systems, Inc, Natick, Mass.). Serum chemistry tests were performed by the University of Iowa Clinical Laboratories.

Glucose Tolerance Tests

Mice were fasted overnight but permitted access to water. A dose of 2 grams/kg (200 μl /20 gram of body weight of a 20% glucose solution) was administered intraperitoneally to unsedated mice. Blood samples were taken from a nick in the tail vein and drawn by capillary action into microcuvettes (B-glucose HemoCue Microcuvettes, Angelholm, Sweden), and placed into a B-Glucose Analyzer (HemoCue, Angelhom, Sweden). Time points for measurement included: baseline, 30 min, 60 min, 90 min, and 120 min.

Electrophysiology

Chloride ion currents were measured from aortic vascular smooth muscle cells at room temperature (22-24° C.) using either standard whole-cell voltage-clamp techniques (Hamill et al., 1981) or perforated patch recording (Horn adn Marty, 1988) performed with an Axopatch 200B patch-clamp amplifier driven by pClamp 7 software (Axon Instruments, Foster City, Calif.). Pipette resistances were 3-5 MOhms.

The hypotonic (255 mOsm/kg by freezing point depression (Osmette, Precision Systems Inc, Natick, Mass.) bath solution contained (mM): NaCl 125, $MgCl_2$ 2.5, $CaCl_2$ 2.5, HEPES 10, glucose 5.5, pH 7.2 with NaOH. Isotonic bath solution had the same ionic composition as the hypotonic solution except that the osmolality was adjusted to 305 mOsm/kg by adding mannitol. Pipette solution for whole cell recording contained (mM): N'-methyl-D-glucamine chloride (NMDG-Cl) 135, EGTA 2, Mg-ATP 5, HEPES 10, pH 7.2 with NMDG base. Pipette solution for perforated-patch recording contained (mM): CsCl 130, $MgCl_2$ 2.5, HEPES 10, pH 7.2 with CsOH. Osmolality of both pipette solutions was adjusted to 305 Osm/kg by adding mannitol. Chloride equilibrium potential remained at 0 mV under both isotonic and hypotonic conditions. All currents were normalized to cell membrane capacitance and expressed as current density (pA/pF). Amphotericin was first dissolved in DMSO at a concentration of 60 mg/ml and then 20 μl of this solution was mixed with 5 ml of pipette solution by vortexing. All components of the buffer solutions were obtained from Sigma.

Mutation Analysis in Human Subjects

Informed consent was obtained from all study patients or their legal guardians. This consent form was approved by the University of Iowa Institutional Review Board. Eighty-one probands with Leber Congenital Amaurosis (LCA), and 92 patients with retinitis pigmentosa (RP) were ascertained from the United States and Canada. DNA was extracted from peripheral blood using a previously described protocol (Buffone and Darlington, 1985). All probands were screened for mutations in the coding sequence of the ClCN3 gene with single strand conformation polymorphism (SSCP) analysis. Ninety-three control subjects from Iowa were screened in an identical fashion. The primer sequences used for SSCP of 22 amplimers were derived from flanking introns and are available from the authors upon request. The PCR amplification products were denatured for 3 min at 94° C. and then electrophoresed on 6% polyacrylamide +5% glycerol gels at 25 W for 3 hours. Gels were stained with silver nitrate (Orita et al., 1989; Sheffield et al., 1993). PCR products from samples with aberrant electrophoretic patterns were then sequenced bidirectionally with fluorescent dideoxynucleotides on an ABI model 377 automated sequencer.

Statistics

Comparisons between different groups of animals were performed by one-way ANOVA, with Dunnett's test for multiple comparisons when the F statistic was significant ($P<0.05$). T-tests were used when only two groups were compared. The numbers of mice born with each genotype were compared to the expected Mendelian ratios using the Chi-square test. Proportions of mice in each group exhibiting a characteristic (e.g., survival to a time point) were compared using z-tests. $P<0.05$ is taken as significant. Values are expressed as the mean±SEM.

Results

Disruption of the Murine Clcn3 Gene and Generation of Clcn3$^{-/-}$ Mice

Figure 4A:
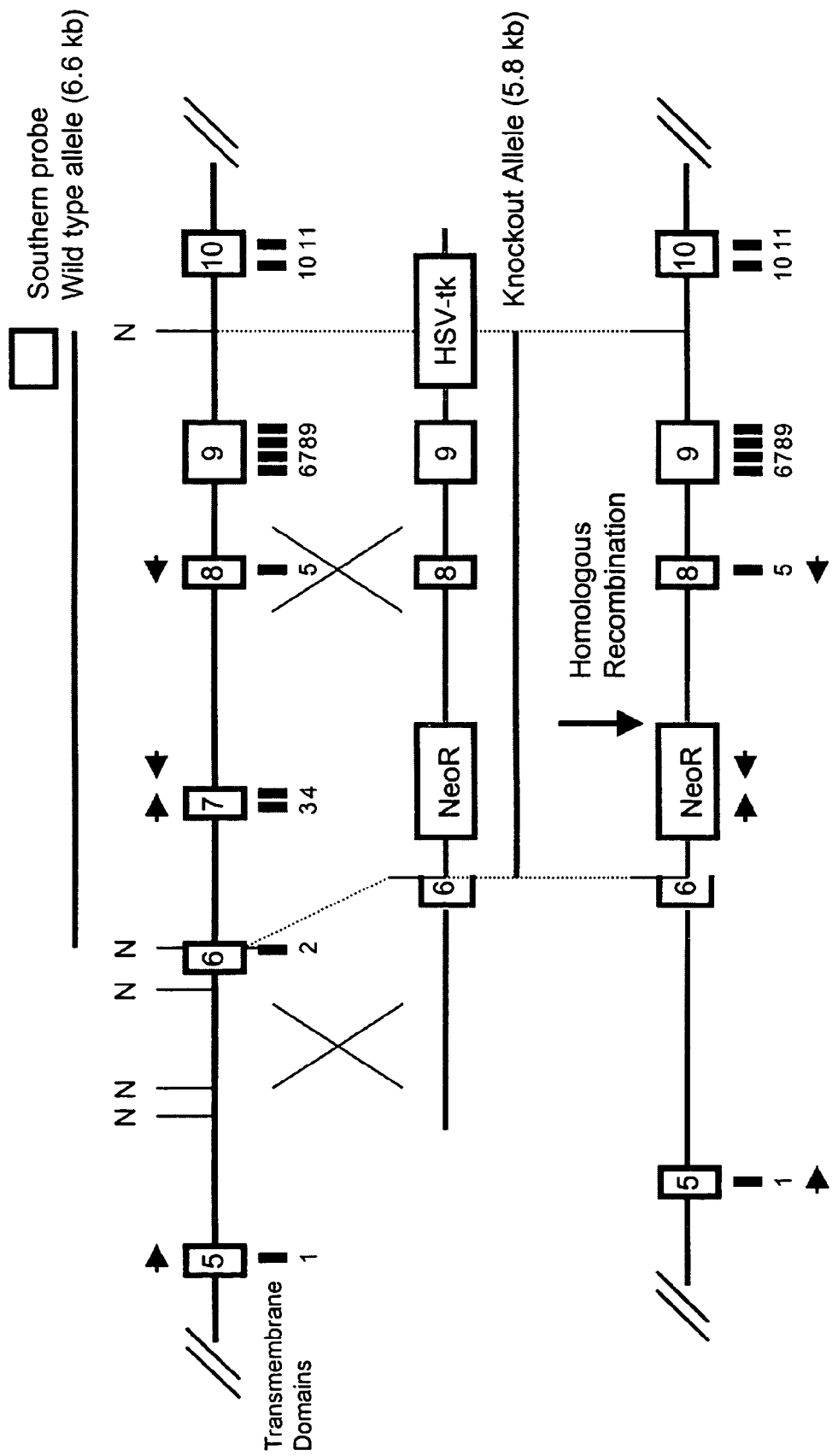
FIG. 4 depicts the targeted inactivation of the Clcn3 gene. (A) shows the structure of the Clcn3 gene for exons 5 through 10, the replacement vector and the targeted allele. The knockout allele replaces 13 bp of exon 6 and all of exon 7 with vector sequence including the neomycin resistance gene (NeoR). (B) shows Southern blot analysis of embryonic stem (ES) cells. When genomic DNA was digested with the restriction enzyme NheI (N), the probe (open rectangle at top) detected a 6.6 kb fragment representing the wild type allele and a 5.8 kb fragment for the knockout allele; (C) shows the genotyping of mice by PCR. Mice homozygous for the knockout allele (−/−), heterozygous (+/−) and homozygous for the wild type (+/+) were identified by PCR amplified from mouse genomic DNA using primers specific for the wild type Clcn3 gene (Exon 7) and the neomycin resistance gene (Neo), respectively. A 100 bp ladder is included as a size standard (M); (D) shows the genotyping of mice by RT-PCR. The mouse Clcn3 genotypes were also determined by PCR amplification of mouse cDNA using primers that flank exons 6 and 7, such that the forward primer was derived from exon 5 and the reverse primer from exon 8. Exons 6 and 7 are present in the wild type allele (554), but are spliced out of the transcript along with the Neo gene in the knockout allele (224); (E) shows the genotyping of ES cells by RT-PCR. Embryonic cells were genotyped by RT-PCR as described in ID. Duplicate experiments were run with (+) and without (−) reverse transcriptase (RT) as a control.

A null mutation in the Clcn3 gene was generated by replacing part of exon 6 and all of exon 7 with a cassette containing the neomycin resistance gene (FIG. 4A). Appropriate gene targeting was detected by Southern blot analysis (FIG. 4B) in 2 of 69 colonies surviving double selection. Both lines of chimeras transmitted the ES genome to the next generation when bred to C57BL/6J females. Heterozygous F1 hybrids from chimera breeding were intercrossed to generate homozygotes. The knockout and wild type alleles were detected by PCR using primers specific for the neomycin resistance gene and exon 7, respectively (FIG. 4C). In addition, since the splice donor site for exon 6 is missing in the knockout allele, its processed message is predicted to lack exons 6 and 7. Using a forward primer from exon 5 and a reverse primer from exon 8 a smaller product was amplified from cDNA derived from mice that carry the knockout allele (FIG. 4D). This suggested that the knockout animals were splicing out the remainder of exon 6, and the neomycin resistance gene, and creating message that skipped from exon 5 to exon 8. DNA sequence analysis of the amplified products verified that the smaller product indeed lacked exons 6 and 7 (data not shown). Although splicing from exon 5 to 8 creates a message that remains in the same reading frame, exons 6 and 7 contain transmembrane domains 2, 3 and 4. Transmembrane domain 2 is critical for function of CLCN5, another member of the ClC chloride channel family (Lloyd et al., 1996), suggesting that any product made from this Clcn3 knockout allele is not a functional channel. The lack of any identifiable phenotype in the Clcn3$^{+/-}$ mice also suggests that this mutated ClC-3 protein is not able to interact with normal ClC-3 monomers and disrupt function by acting as a dominant negative mutation. FIG. 4E shows RT-PCR confirmation of the genotype of the Clcn3$^{-/-}$ ES cells using the same primers as were used in FIG. 4D. Images of some gels were cropped so that relevant samples appear in adjacent lanes.

When 578 intercross progeny from 79 litters were genotyped, the ratio of Clcn3$^{+/+}$, Clcn3$^{+/-}$ and Clcn3$^{-/-}$ mice (127, 330, 121) resulting from Clcn3$^{+/-}$×Clcn3$^{+/-}$ breedings was not statistically different than expected from predicted Mendelian ratios, demonstrating that the Clcn3 gene is not required for viability at birth. Some, but not all, male Clcn3$^{-/-}$ mice successfully fathered litters that contained normal numbers of healthy pups. Only one litter was documented from matings involving Clcn3$^{-/-}$ females and Clcn3$^{+/-}$ males. That litter of four pups died shortly after birth.

General Appearance, Growths Survival, and Behavior

Figure 5A:
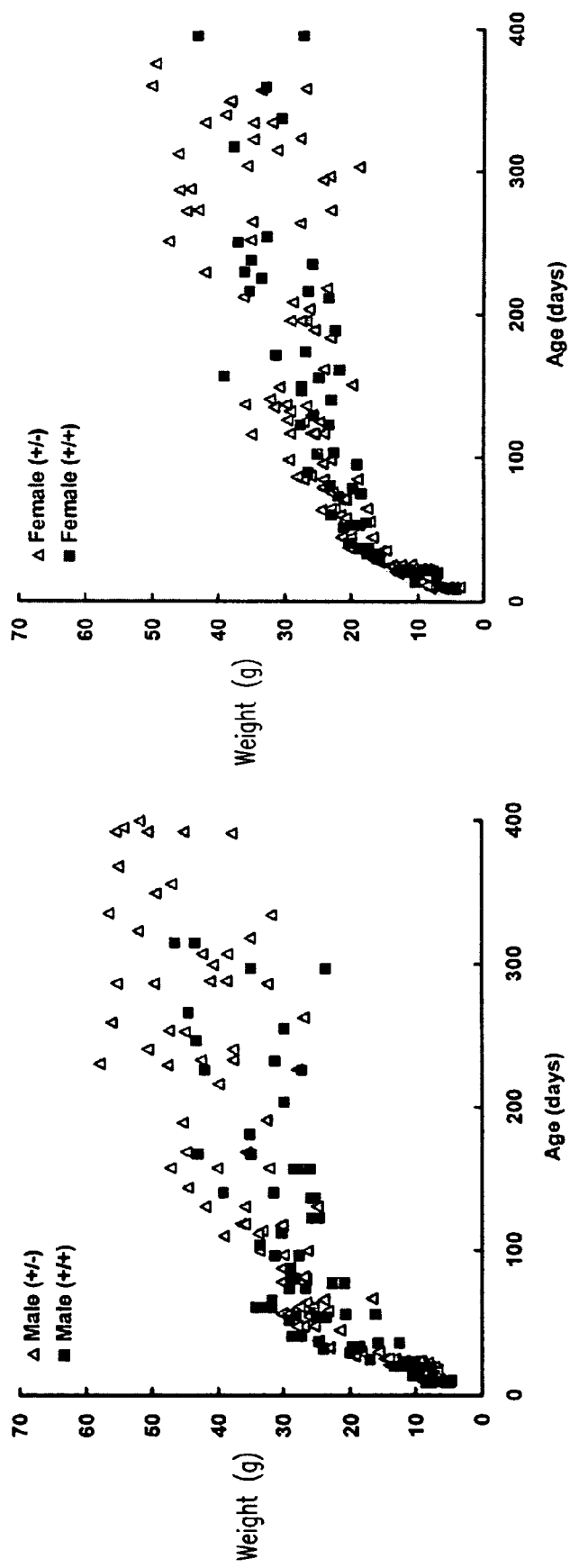
FIG. 5 shows the growth and survival of $Clcn3^{-/-}$ mice compared to $Clcn3^{+/-}$ and $Clcn3^{+/+}$ littermates. Growth of heterozygote mice is not different from wild type mice (A); compared to heterozygote littermates, the weight of knockout mice is diminished substantially at the time of tail sample collection (~10 days) and at all time points thereafter (B); high mortality rate in the first ten months of life in knockout mice compared to heterozygotes. There are no gender-based differences in $Clcn3^{-/-}$ mortality rates (C).
Figure 5B:
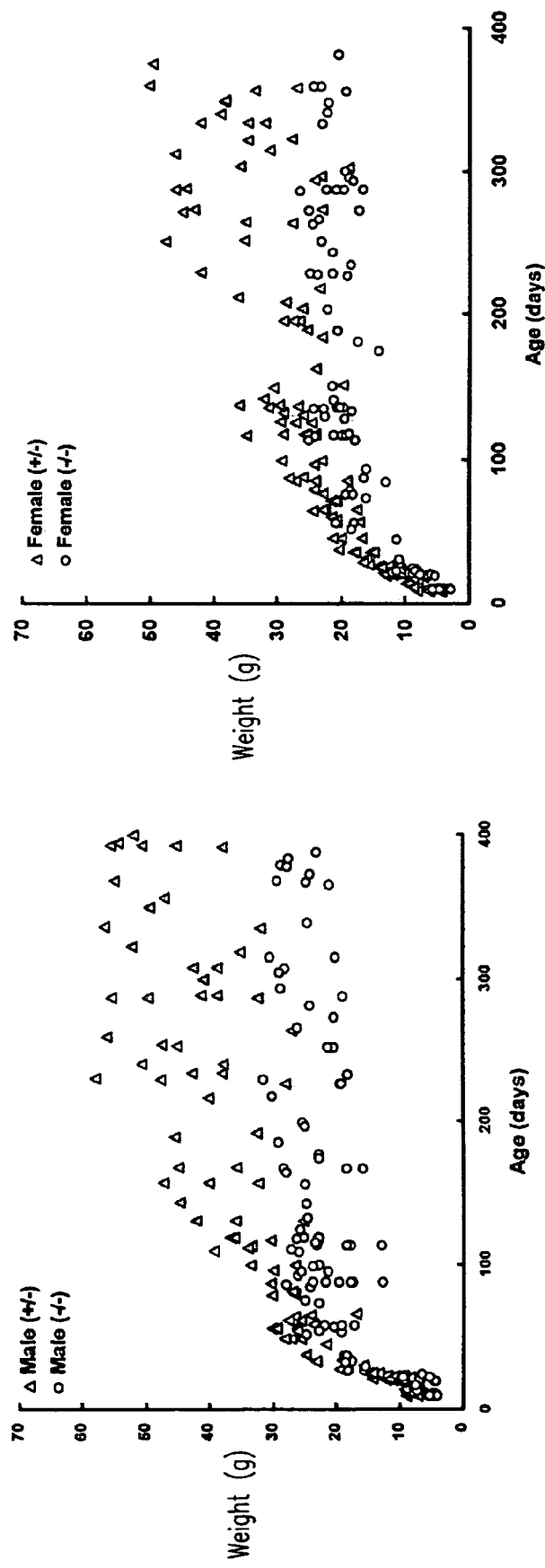
Figure 5C:
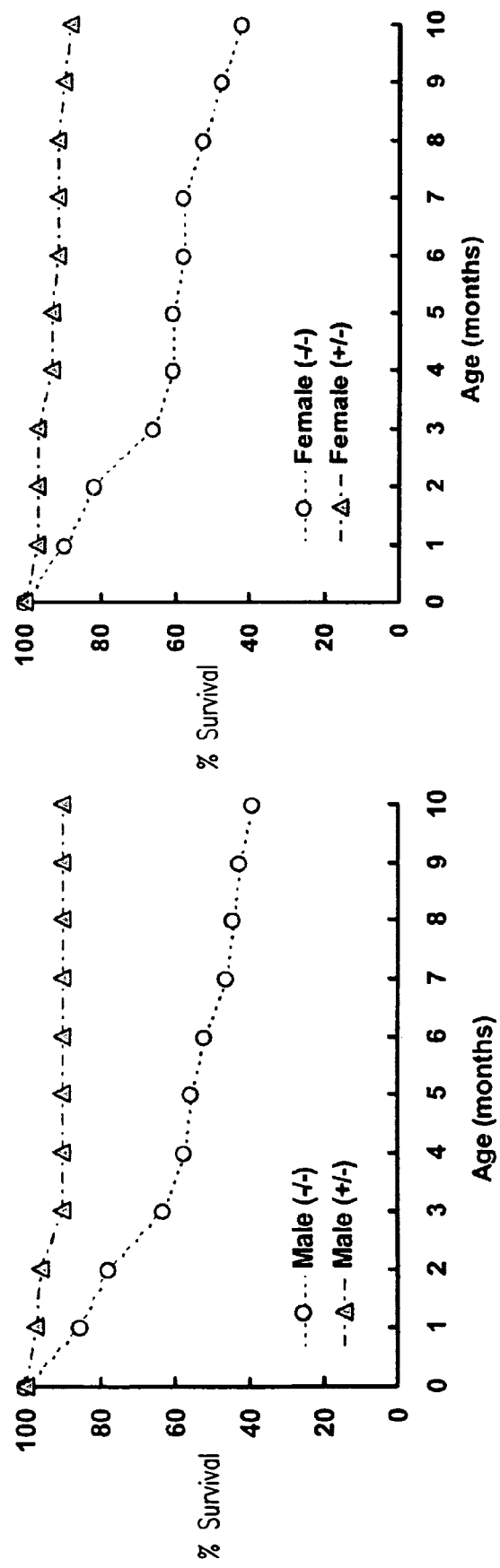

Both the growth and survival of Clcn3$^{-/-}$ mice were impaired substantially compared to age- and gender-matched Clcn3$^{+/-}$ and Clcn3$^{+/+}$ mice (FIG. 5). There was no difference in the growth (FIG. 5A) or survival for Clcn3$^{+/-}$ mice compared to Clcn3$^{+/+}$ mice (survival data for wild types not shown). Male and female Clcn3$^{+/-}$ and Clcn3$^{+/+}$ mice continued to gain weight throughout the first six months of life. As can be seen in FIG. 5, adult male Clcn3$^{-/-}$ mice rarely exceeded 30 grams, and female Clcn3$^{-/-}$ mice rarely exceeded 25 grams. There was a striking absence of fat in the abdominal and other body cavities in adult Clcn3$^{-/-}$ mice compared to similar-aged Clcn3$^{+/-}$ controls. The weight difference between knockout mice and their littermates was apparent and significant (P<0.05) as early as PD9-PD11 for both males: knockouts 4.5±0.2 g, (n=23); heterozygotes 6.7±0.3 g, (n=25); wild type 6.1±0.2 g, (n=25) and females: knockouts 4.5±0.3 g (n=22); heterozygotes 6.2±0.4 g (n=23); wild type 5.9±0.3 g (n=23).

Knockout mice died prematurely and unexpectedly (FIG. 5C) without any obvious prodrome of illness. The death rate is fairly constant throughout the first 10 months of life and is not increased during the first two months of life when rapid degenerative changes are occurring in the hippocampus and retina. By three months, one-third of all knockout mice had died, and by six months half were dead. No gender-related differences in survival were seen at any time point during the first ten months of life.

Figure 6:
FIG. 6 shows priapism in an adult $Clcn3^{-/-}$ mouse.

Priapism was frequently observed (FIG. 6) in Clcn3$^{-/-}$ males but never in Clcn3$^{+/-}$ or Clcn3$^{+/+}$ animals. Priapism was observed in mice as young as 8 weeks but was more common in older mice. Table 1 characterizes observations of all knockout males in the colony older than 6 months of age observed at intervals during one month. A plus sign indicates the presence of priapism at an independent observation time, a minus sign indicates its absence. Episodes lasted from hours to days. We evaluated the histology of the corpus cavernosum in 5 knockouts and 5 controls, including one young mouse (age, 53 days) that was sacrificed while exhibiting priapism. No obvious differences were observed at the light microscopic level (H&E staining, data not shown).

TABLE 1

| Age, days | Day 0 midday | Day 8 a.m. | Day 13 midday | Day 13 5 pm | Day 14 noon | Day 14 8 pm | Day 15 noon | Day 15 11 pm | Day 16 midday | Day 18 midday | Day 27 noon | Day 28 noon | Day 29 noon |
|---|---|---|---|---|---|---|---|---|---|---|---|---|---|
| 199 | n | n | n | n | y | n | n | n | n | n | n | n | n |
| 199 | n | n | n | n | n | n | n | n | n | n | n | n | n |
| 191 | n | y | y | y | n | n | n | n | n | n | n | y | y |
| 238 | y | y | y | y | y | y | y | y | y | y | y | y | y |
| 271 | n | y | n | n | n | n | n | n | n | n | n | n | n |
| 248 | n | n | n | n | n | n | n | n | n | n | n | n | n |
| 328 | n | y | n | n | n | n | n | n | n | n | n | n | n |
| 210 | n | n | n | n | n | n | n | n | n | n | n | n | n |
| 210 | nd | n | n | n | n | n | n | n | n | n | n | n | n |
| 188 | n | n | n | n | n | n | n | n | n | n | n | n | n |
| 188 | y | n | n | n | n | n | n | n | n | n | n | n | n |
| 374 | n | n | n | n | n | n | n | n | n | n | n | n | n |
| 293 | y | n | y | y | y | y | y | y | y | died | | | |

In general, Clcn3$^{-/-}$ mice tended to appear jittery, and walked with a waddling gait. These abnormalities were seen even at very early ages (2-3 weeks), prior to severe hippocampal and retinal degeneration. Adult Clcn3$^{-/-}$ mice exhibited a prolonged recovery time from benzodiazepines (midazolam) and barbiturates (pentobarbital). Even at reduced doses, there was an increased incidence of death from pentobarbital.

When the tail is elevated in conscious mice, the normal response (FIG. 7A) is to splay the limbs (especially the hindlimbs) in a behavior termed "escape extension" (Lewis et al., 2000). When Clcn3$^{-/-}$ mice were suspended by the tail, an abnormal rear leg-folding behavior (FIG. 7B and 7C) was exhibited within 30 seconds by 10 of 15 (66.7%) of knockouts, 1 of 17 (3.9%) heterozygotes, and 0 of 9 wild types. Within 1 minute 12 of 15 (80%) knockout mice exhibited this behavior, and there was no change in the response rate for Clcn3$^{+/-}$ or Clcn3$^{+/+}$ mice. At both 30 and 60 seconds, the proportion of knockouts exhibiting this behavior was statistically greater than in the control groups (P<0.05).

Figure 7:
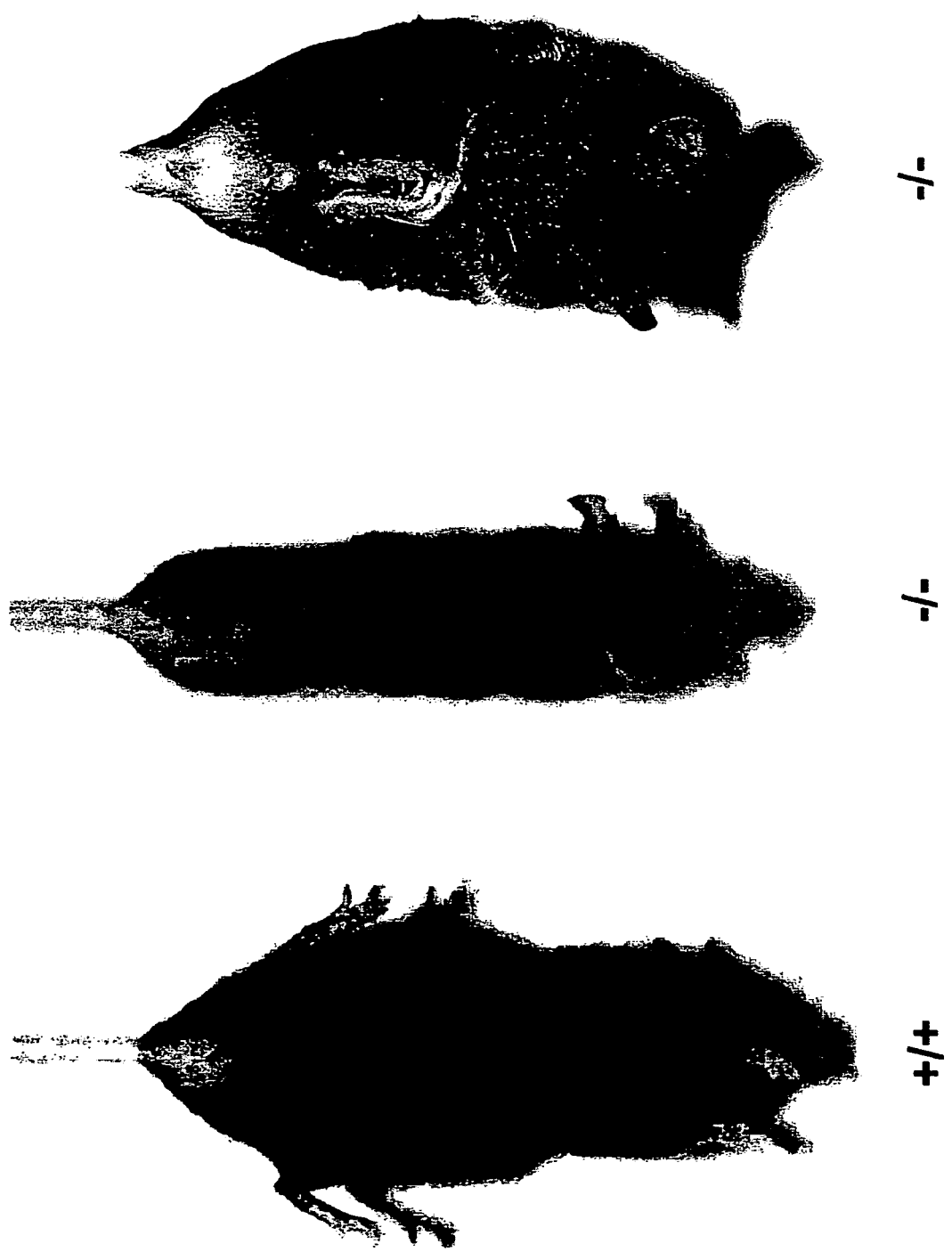
FIG. 7 shows an abnormal hindlimb grasp observed in $Clcn3^{-/-}$ mice, representing the absence of the escape extension response displayed upon tail elevation in normal mice. Heterozygote mouse exhibits normal splaying of the hindlimbs when suspended by the tail, in a response identical to that seen in wild type mice (A); knockout mouse folds its hindlimbs towards the midline of the body when suspended by the tail. Most $Clcn3^{-/-}$ mice display this pattern of abnormal rear leg-folding behavior (B); upon tail suspension, a few knockout mice not only fold their rear legs but also their forelimbs, and curl their bodies into a "fetal" position (C).
Figures 8A, 8B, 8C:
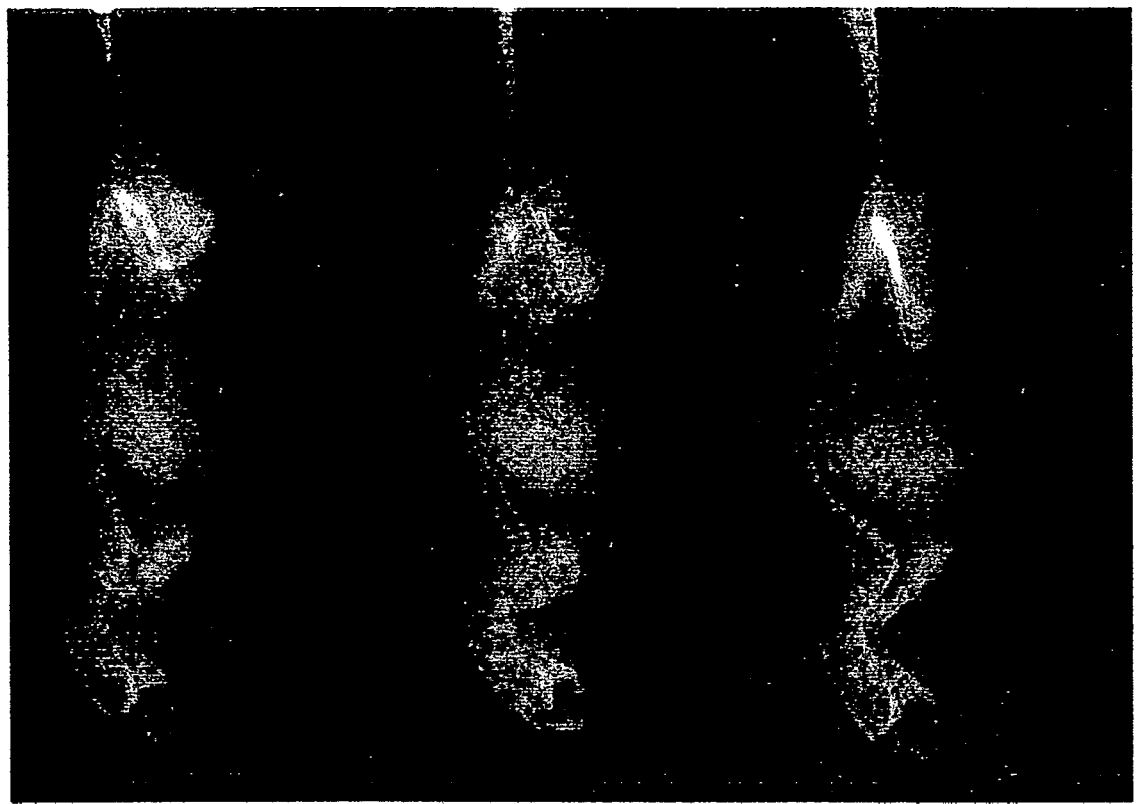
FIG. 8 shows lateral view X-rays, illustrating kyphosis in $Clcn3^{-/-}$ mice compared to controls. Typical normal heterozygote mouse (A); knockout mouse exhibiting typical curvatures of thoracolumbar and cervicothoracic spine (B); more severely affected knockout mouse (C); adult $Clcn3^{+/-}$ mouse with normal spine conformation (D); and adult $Clcn3^{-/-}$ mouse (a littermate of D) displaying marked kyphosis (E).
Figure 8D:
Figure 8E:
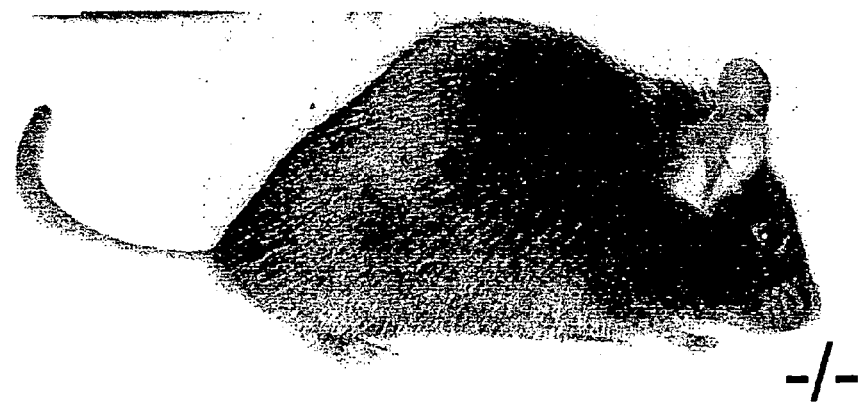

Gross physical observation of the Clcn3$^{-/-}$ mice showed a marked 'hunchback' appearance, and post-mortem dissection seemed to indicate substantial anterior-posterior curvature of the spine in Clcn3$^{-/-}$ mice. Lateral plane X-rays (FIG. 8) revealed that both the thoracolumbar (Clcn3$^{-/-}$; 140±3.3 degrees (n=12), Clcn3$^{+/-}$; 156±1.9 degrees (n=13), P<0.05) and cervicothoracic (Clcn3$^{-/-}$; 125±3.4 degrees, Clcn3$^{+/-}$; 135±1.7 degrees, P<0.05) angles were significantly different compared to littermate or age and gender-matched controls. Heterozygote and knockout mice selected for FIGS. 8A and 8B, respectively, represented individuals with anterior-posterior curvatures close to their group averages, whereas FIG. 7C shows an example of a Clcn3$^{-/-}$ mouse with more severe curvature. Comparable measurements were made on frontal plane X-rays to assess the presence of scoliosis, but yielded no differences between groups.

Coat color in the Clcn3 colony varied from pale gray to black, as is expected in this mixed genetic background. However, as the Clcn3$^{-/-}$ mice aged they frequently developed a marked lightening of the fur on the caudal half of their body. This was particularly evident in mice with black coats. This transition in color occurred in both female (FIG. 7B), and male (8E) mice, and was approximately circumferential with an irregular border occurring at about the mid-abdomen. This change in coat color was never observed in Clcn3$^{+/+}$ or Clcn3$^{+/-}$ mice.

Muscle Histology

Diaphragm and skeletal muscle tissues were examined in order to determine if kyphosis was secondary to muscular dysplasia or dystrophy. Hindlimb skeletal muscle samples from 9 knockout mice, 7 heterozygotes, and 5 wild type mice were fixed, sectioned, stained with H&E, and examined by light microscropy. Diaphragm muscle was examined in 7 of these mice. Nine hindlimb specimens were from 'weanling' mice (age 22-33 days), 7 from young adults (53-126 days), and 5 from aged adults (316-556 days). No evidence of myopathic changes was seen by light microscopy (data not shown).

Central Nervous System Histology

Figure 9:
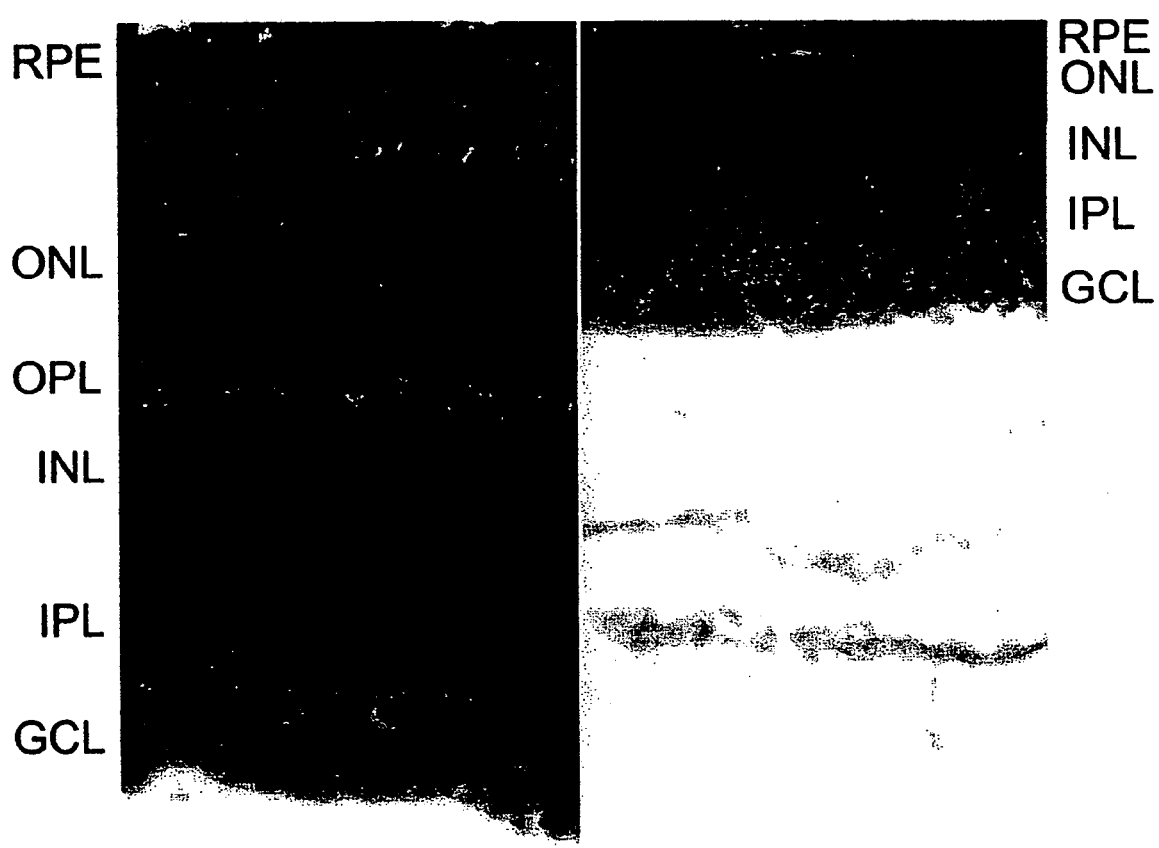
FIG. 9 shows retinal histology (H&E, both sections 40X) (RPE, retinal pigmented epithelium; ONL, outer nuclear layer; OPL, outer plexiform layer; INL, inner nuclear layer; IPL, inner plexiform layer; GCL, ganglion cell layer). Cross-section of normal retina from a 23-day old $Clcn^{+/+}$ mouse (A); and (B) shows the retina from a 23-day old $Clcn3^{-/-}$ mouse (littermate of mouse shown in part A) showing marked degeneration and greatly reduced numbers of cells in the photoreceptor layer (ONL), with complete absence of the outer segments. There are greatly reduced numbers of cells in other layers. No retinal abnormalities were observed in $Clcn3^{+/-}$ mice.

H&E stained sections were examined of eyes from 5 Clcn$^{-/-}$, 4 Clcn$^{+/-}$, and 4 Clcn$^{+/+}$ mice, using littermates or age-matched controls when a littermate was not available. In Clcn3$^{-/-}$ mice there was a rapid, progressive postnatal degeneration of the retinal photoreceptors, culminating in complete loss of the photoreceptor layer, as shown in FIG. 9. Retinas from heterozygote mice were histologically normal. Details of the postnatal time course of anatomical and functional retinal degeneration were similar to those described previously (Stobrawa et al., 2001). The functional blindness of Clcn3$^{-/-}$ mice was confirmed, as indicated by the absence of both wave a and wave b in flash electroretinograms from two adult knockout mice (ages: 118, 191 days) which had been dark-adapted overnight (data not shown).

Clcn3$^{-/-}$ mice exhibited a profound, postnatal loss of neurons from the hippocampal formation. This loss of hippocampal neurons was progressive, with a time course that depended on position along the septo-temporal axis of the hippocampal formation. In contrast, brains of Clcn3$^{+/-}$ mice appeared neuroanatomically normal at all time points examined. No degenerative processes or abnormalities of neural anatomy or development were evident in Clcn3$^{+/-}$ or Clcn3$^{+/+}$ mice.

Figure 10:
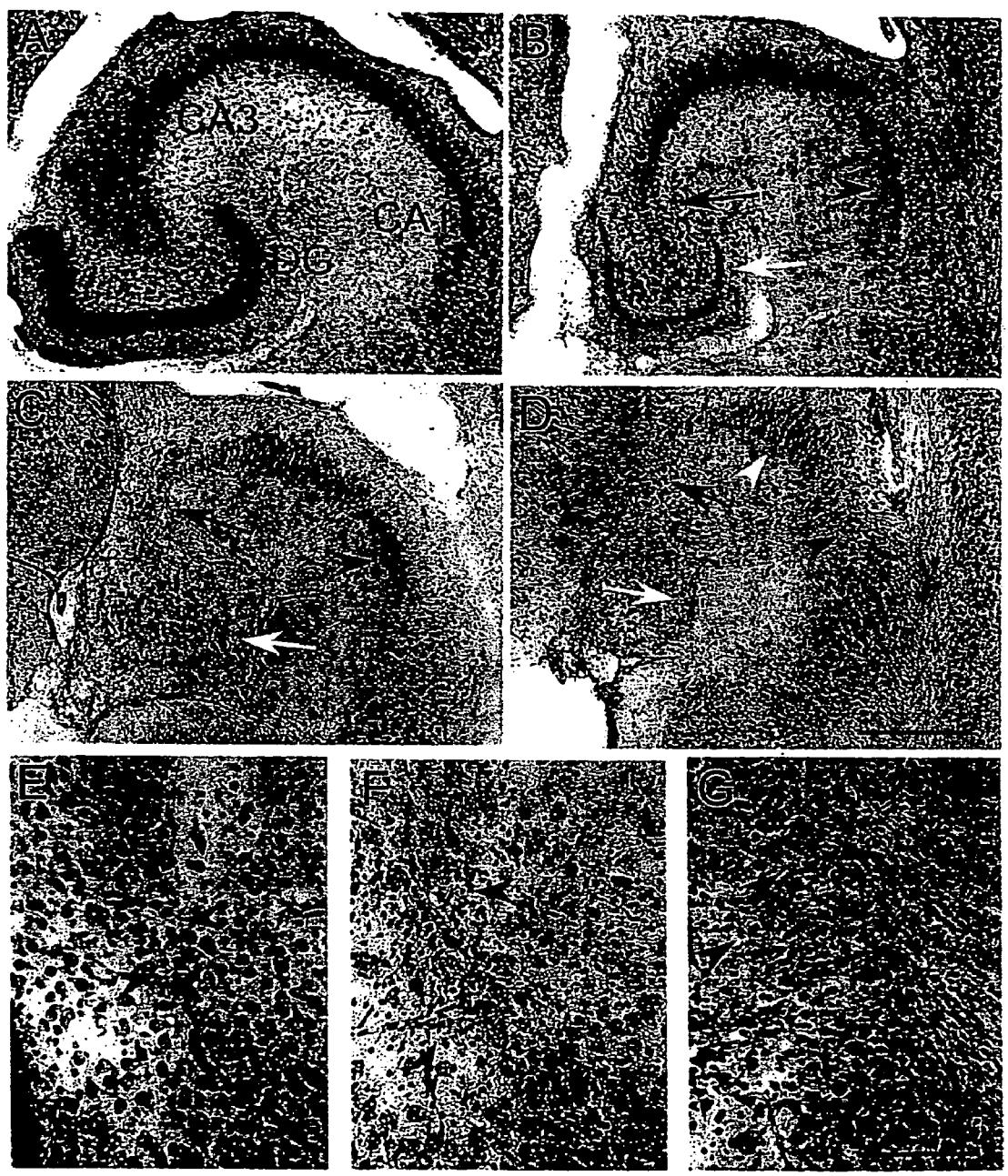
FIG. 10 shows Nissl-stained horizontal sections demonstrating the progressive neuronal loss (A-D) and gliosis (E-G) within the posterior hippocampal formation of $Clcn3^{-/-}$ mice. Calibration bar in D represents 400 µm in A, B, C and D. Bar in G represents 60 µm in E, F, and G. On PD23, the hippocampal formation appears normal. A full complement of granule cells and pyramidal cells has been generated. The cells have a normal cytoarchitectural arrangement, and no evident loss of neurons has yet occurred. The dentate gyrus (DG), CA3 pyramidal cells, and CA1 pyramidal cells are labeled (A); by PD75 (2.5 months), there is a substantial loss of granule cells from the dentate gyrus (white arrow). Near the hilus, there has been some dropout of CA3 pyramidal cells (black arrow). However, the majority of pyramidal cells in both CA3 and CA1 (arrowhead) remain alive at this time point (B); by PD165 (5.5 months), loss of dentate granule cells has progressed (white arrow). In addition, now there has been a substantial loss of CA3 pyramidal cells (black arrow). Much of the CA1 pyramidal cell population, however, remains intact (arrowhead) (C); by PD270 (9 months), neuronal loss within the hippocampal formation has progressed even further, and is now nearly total. Very few dentate granule cells remain alive (white arrow). Only a small patch of pyramidal cells can be identified (white arrowhead). The extensive pyramidal cell loss at this stage includes not only the CA3 subregion (black arrow), but also CA1 (black arrowhead) (D); insert from (B) demonstrates the beginnings of gliosis at age 2.5 months. The small darkly-stained cells with little cytoplasm (arrowheads) are astrocytes that are replacing lost neurons (E); insert from (C) demonstrates that the density of glial cells (arrowheads) within the hippocampus has increased markedly by 5.5 months of age (F); insert from (D) demonstrates that a dense glial scar (arrowheads) has replaced the neuronal populations of the hippocampal formation by 9 months of age (G).
Figure 11:
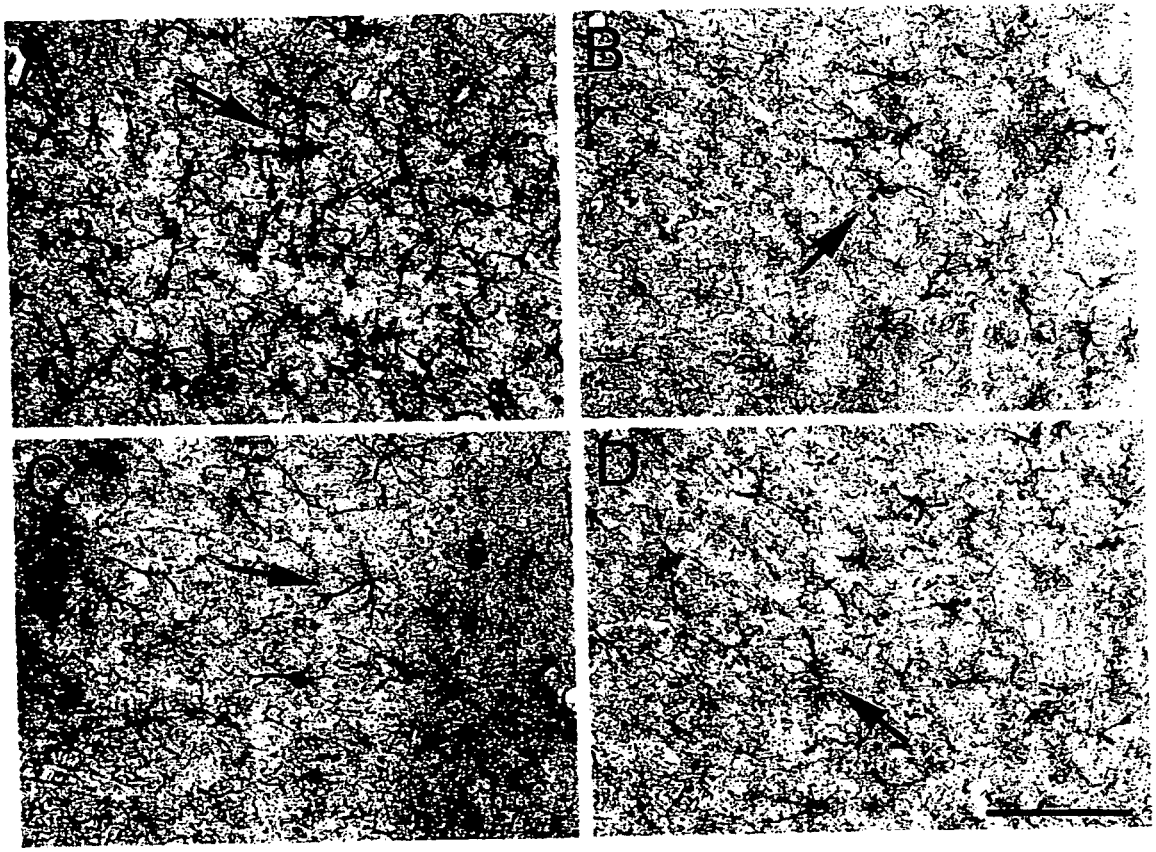
FIG. 11 depicts photomicrographs of sections through the hippocampus and cerebral cortex stained immunohistochemically for glial fibrillary acidic protein (GFAP), a specific marker of astroglial cells. The sections were all derived from animals on PD165 and reveal an astrogliosis in the hippocampal formation of $Clc3n^{-/-}$ mice. In each panel, the arrow points to an immunohistochemically labeled astrocyte. Calibration bar in D represents 40 µm in A, B, C, and D. (A) is a section through the dentate gyrus of a knockout mouse. Note that the density of astrocytes in the dentate gyrus of the knockout mouse is much greater than in the wild type mouse (B); (B) is a section through the dentate gyrus of wild type mouse; (C) is a section through the cerebral neocortex of a knockout mouse; and (D) is a section through the cerebral neocortex of a wild type mouse. In the cerebral neocortex of the knockout mouse, the density of astrocytes is similar to that of the wild type mouse. No astrogliosis occurs in the neocortex of knockout or wild type mice. These results demonstrate that an astrogliosis occurs in the knockout mice, but only in the hippocampal formation, where the astroglial response accompanies neuronal loss.

The structure of the hippocampal formation and of all other brain regions within the knockout mice appeared normal at PD 23 (FIG. 10A), indicating that these animals generate a normal complement of hippocampal neurons during prenatal and early postnatal life. However, by PD75 (FIG. 10B), a loss of neurons is evident in the hippocampal formation. At this time point, the neuronal dropout is most severe among the granule cells of the dentate gyrus. This loss of dentate granule cells substantially reduces the width of the dentate stratum granulosum. By PD165 (FIGT. 10C), neuronal dropout from the hippocampal formation has substantially worsened and involves not only granule cells, but also pyramidal cells. However, at this time point the loss of pyramidal cells is more severe within the CA3 region than within CA1. In addition to neuronal loss, a second pathologic process, gliosis, is also evident at this age. Within the regions in which neurons are lost, large numbers of small darkly-staining cells are apparent in the Nissl-stained sections. The identity of these cells was further confirmed in sections immunohistochemically stained for glial fibrillary acidic protein (GFAP), an astrocyte-specific marker. As shown in FIG. 11, the small cells contain GFAP, and the density of these labeled cells is substantially greater in the Clcn3$^{-/-}$ hippocampus than in the control hippocampus. By PD270 (FIG. 10D), the loss of neurons from the hippocampal formation is profound. A large proportion of the neurons have been replaced by astrocytes (FIG. 10E-10G). In contrast to the pattern evident at earlier time points, pyramidal cell loss is now extensive, not only in the CA3 subpopulation, but also in CA1.

Figure 12:
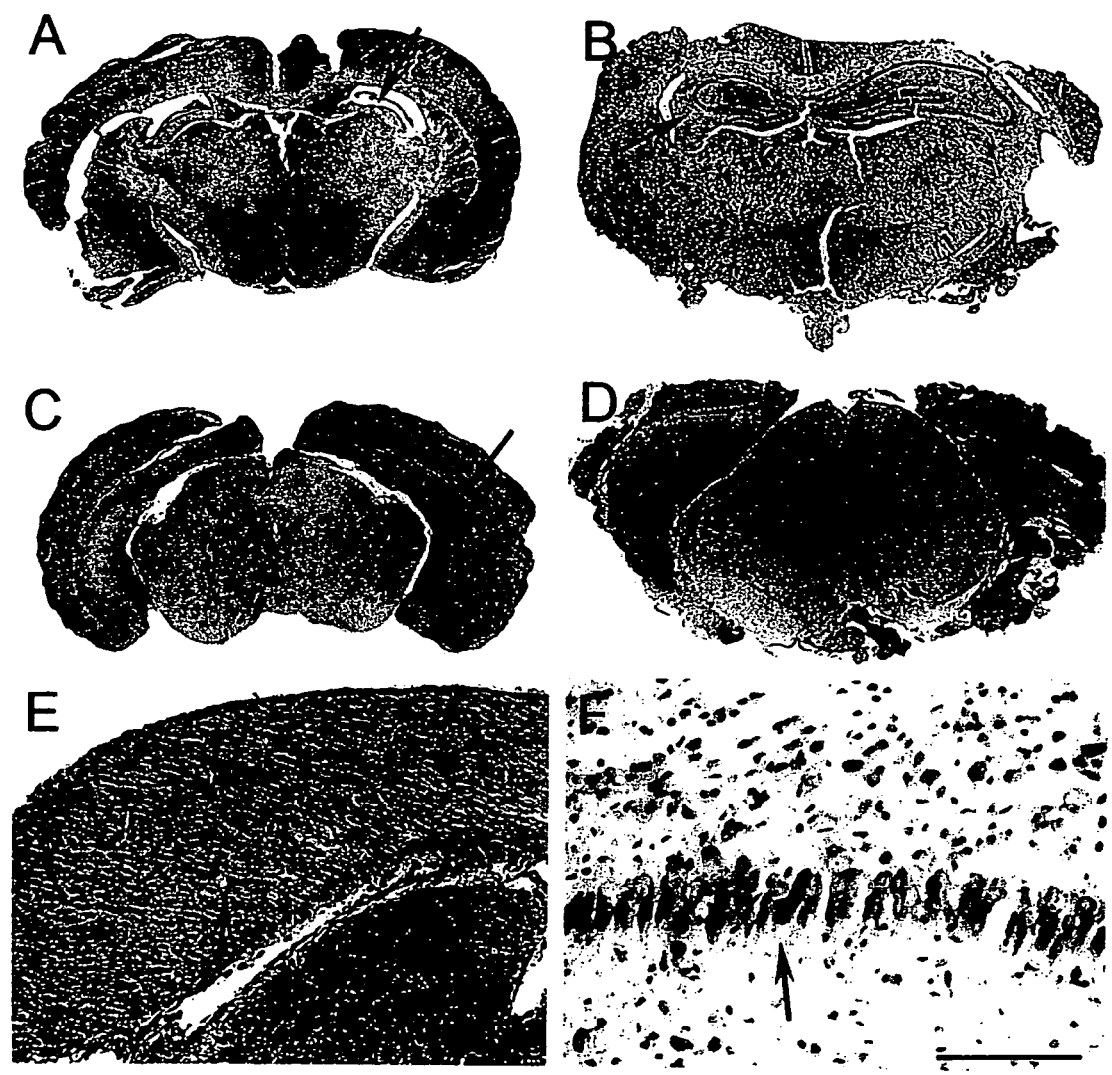
FIG. 12 shows Nissl-stained coronal sections through the cerebrum demonstrating that neuronal loss in the anterior hippocampal formation precedes neuronal loss in its posterior regions. All sections are taken from adult mice at the age of 11 months. Magnification bar in F represents 1.6 mm in A and C, 1.45 mm in B and D, 70 µm in E, and 30 µm in F. (A) is a section through the anterior forebrain of a $Clcn3^{-/-}$ mouse demonstrating that all neurons of the anterior hippocampus (arrow) have degenerated and that the hippocampus is markedly atrophied; (B) is a section through the anterior forebrain of a $Clcn3^{+/+}$ animal taken from the same anterior-posterior position as in (A), demonstrating the normal configuration of neurons within the hippocampus (arrow); (C) is a section through the posterior forebrain of a $Clcn3^{-/-}$ mouse demonstrating that some neuronal loss has occurred within the posterior hippocampus, but not to the extent observed more anteriorly. The arrow points to a group of surviving hippocampal pyramidal cells; (D) is a section through the posterior forebrain of a Clcn3$^{+/+}$ mouse demonstrating the normal configuration of hippocampal neurons within the posterior hippocampus (arrow); (E) shows higher magnification of the hippocampus from (A) demonstrating that all neurons of the anterior hippocampus have degenerated and have been replaced by glial cells (arrow); (F) shows higher magnification of the hippocampus from (C) demonstrating that some hippocampal pyramidal cells (arrow) remain alive in the posterior hippocampus at this advanced time point.

Although pathologic changes ultimately occur throughout the hippocampal formation, the time course of the pathology is a function of position along the septo-temporal axis of the hippocampus. As shown in FIG. 12, neuronal call loss occurs earlier and is more severe toward the septal (anterior) pole, than in the temporal (posterior) pole. By PD330 (11 months of age, FIG. 12), the entire anterior portion of the hippocampal formation has undergone neuronal degeneration, and all of the neurons have been replaced with astrocytes. In contrast, in the posterior hippocampus, a group of pyramidal neurons remain identifiable.

Pentylenetetrazole-induced Seizures

Two Clcn3$^{-/-}$ mice (ages: 25, 141 days) were observed having spontaneous generalized tonic-clonic seizures during routine mouse colony care. Spontaneous seizures were never observed in Clcn3$^{+/-}$ or Clcn3$^{+/+}$ mice. Because of these qualitative observations, and more importantly, because hippocampal neuronal loss is often associated with epilepsy and with reduced seizure thresholds, Clcn3$^{-/-}$ mice were hypothesized to have lower thresholds for drug-induced seizure than Clcn3$^{+/-}$ or Clcn3$^{+/+}$ mice. An age of 4-5 weeks was selected, when Clcn3$^{-/-}$ mice still have an essentially intact hippocampus and dentate gyrus, but at a time when neuronal irritability and excitability might be enhanced due to the early phase of neuronal degeneration.

Pentylenetetrazole (PTZ, 70 mg/kg, i.p.), an inhibitor of GABAA receptors (Squires et al., 1984) was administered to conscious, drug-naive mice. PTZ induced generalized seizures in 13/15 (86.7%) Clcn3$^{+/-}$ mice (onset 215±56 sec), in 7/8 (87.5%) of Clcn3$^{+/+}$ mice (onset 280±112 sec), but only 1/8 (12.5%) of Clcn3$^{-/-}$ mice developed seizure activity (onset at 58 sec). One mouse in each of the three groups died during a tonic generalized seizure. Thus, young Clcn3$^{-/-}$ mice are less susceptible to PTZ-induced seizures compared to controls (P<0.05).

Blood Tests

Since ClC-3 is probably most highly expressed at the whole tissue level in the brain and kidney (Weylandt et al., 2001), we performed a series of general screening tests in order to detect any gross abnormalities in renal function as reflected by creatinine clearance, electrolyte balance, and pH regulation. Table 2 shows that no differences in serum Na, K, Cl, HCO$_3$, osmolality, or pH were detected between Clcn3$^{-/-}$ and Clcn3$^{+/-}$ mice. In addition, Clcn3$^{-/-}$ mice showed no abnormality in hematocrit or elevation of creatine kinase, a non-specific indicator of muscle damage. To check specifically for rapid muscle degeneration in early life, we assessed creatine kinase in young mice (average age of Clcn3$^{+/-}$ and Clcn3$^{+/+}$ controls, 62±9 days; Clcn3$^{-/-}$, 69±6 days). As there were no marked differences, this data was grouped with adult mice of all ages (average age of all mice: Clcn3$^{+/-}$ and Clcn3$^{+/+}$ controls, 173±56 days; Clcn3$^{-/-}$, 153±31 days).

TABLE 2

Blood tests in Clcn3$^{-/-}$ and control (Clcn3$^{+/-}$ and Clcn3$^{+/+}$) mice.

| Chemistry | Control | n | Knockout | n |
|---|---|---|---|---|
| Na | 158 ± 2.5 | 4 | 153 ± 2.9 | 5 |
| K | 5.1 ± 0.36 | 3 | 4.9 ± 0.15 | 4 |
| Cl | 122 ± 5.3 | 4 | 120 ± 4.9 | 5 |
| osmolality | 340 ± 13.9 | 8 | 325 ± 7.8 | 6 |
| creatinine | 0.68 ± 0.25 | 4 | 0.36 ± 0.03 | 5 |
| CK(all) | 353 ± 55 | 11 | 284 ± 81 | 11 |
| CK(young) | 332 ± 47 | 8 | 403 ± 134 | 6 |
| Hematocrit | 56 ± 2.3 | 8 | 57 ± 2.9 | 8 |
| Venous Gasses | | | | |
| pH | 7.23 ± 0.02 | 17 | 7.23 ± 0.02 | 8 |
| pCO$_2$ | 46.3 ± 2.4 | 17 | 46.8 ± 3.5 | 8 |
| HCO$_3$ | 19.7 ± 1.3 | 17 | 20.0 ± 1.5 | 8 |

Glucose Tolerance Tests

Figure 13A:
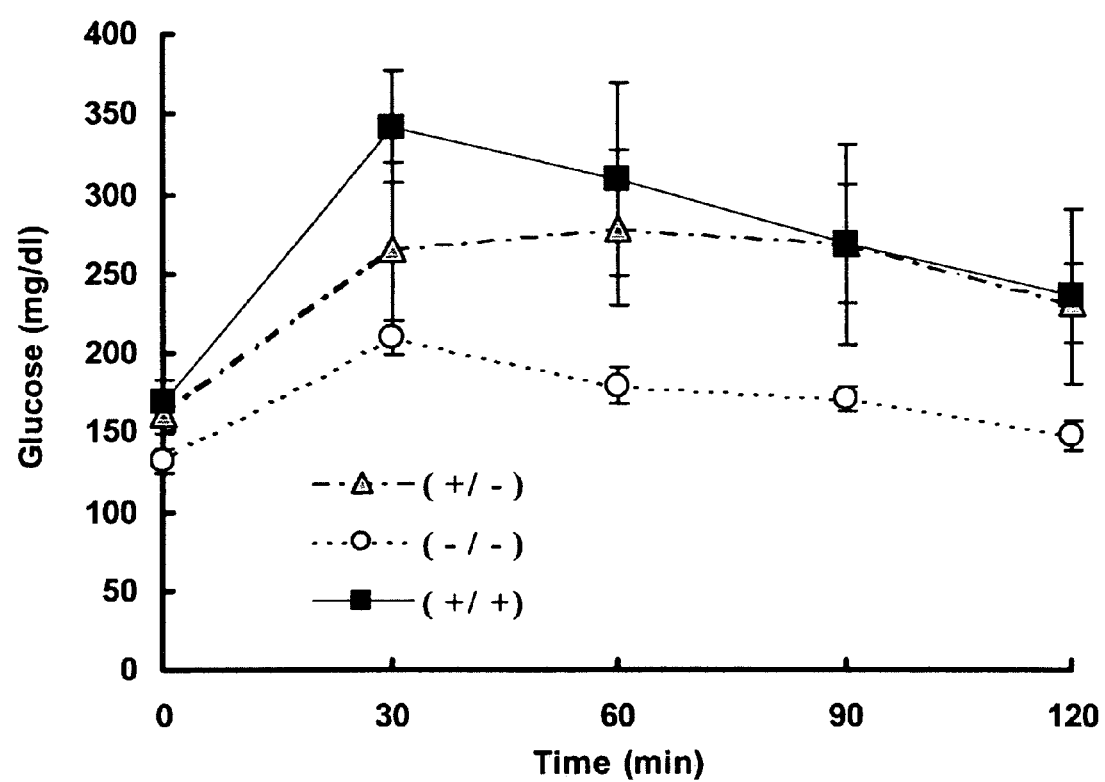
FIG. 13 shows glucose tolerance tests. Time course of response to an intraperitoneal glucose load in knockout, heterozygote, and wild type mice (A); fasting glucose levels (B); and peak glucose levels in response to glucose load (C).
Figure 13B:
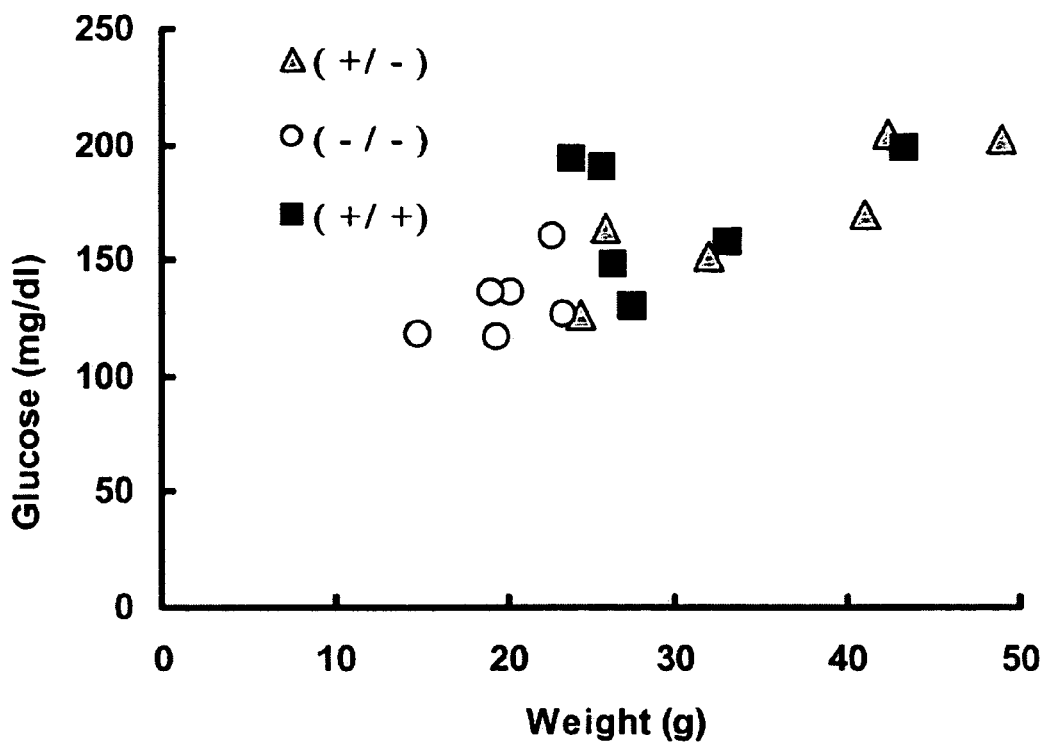
Figure 13C:
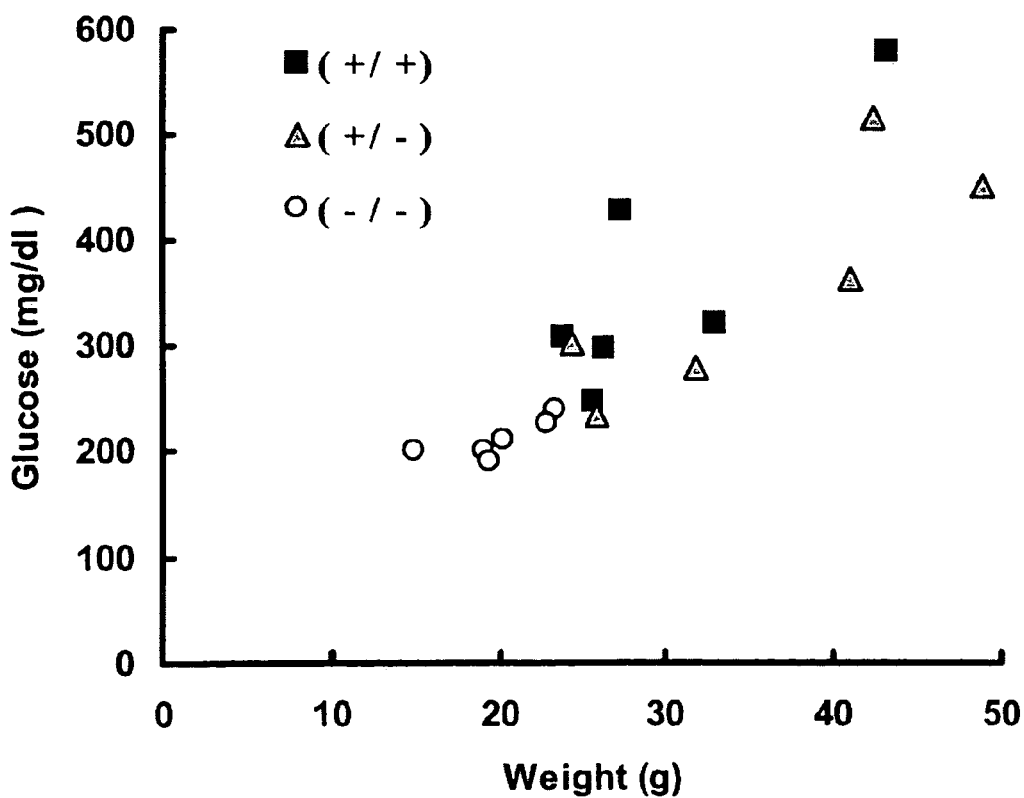

It has been shown that a Cl conductance is important for exocytosis of pancreatic zymogen granules (Thevenod et al. I) and ClC-3 has been proposed as a candidate for this function (Thevenod et al. II). For these reasons we performed glucose tolerance tests on Clcn3$^{+/-}$, Clcn3$^{+/+}$ and Clcn3$^{-/-}$ mice. FIG. 13 demonstrates that fasting blood glucose is actually lower in Clcn3$^{-/-}$ mice (132±7 mg/dl, n=6, P<0.05) than in either control group (Clcn3$^{+/-}$, 170±13 mg/dl, n=6; Clcn3$^{+/+}$, 170±13 mg/dl, n=6). The Clcn3$^{-/-}$ animals also had a lower peak glucose (212±8 mg/dl, P<0.05) compared to either control group (Clcn3$^{+/-}$, 358±48 mg/dl; Clcn3$^{+/+}$, 364±54 mg/dl), and recovered faster after being challenged with an intraperitoneal glucose load. These results are not consistent with an abnormality of either insulin secretion or cellular uptake of glucose. The apparently better glucose tolerance in the Clcn3$^{-/-}$ mice may be related to the fact that these animals are leaner than their age-matched controls.

Electrophysiology

Figure 14:
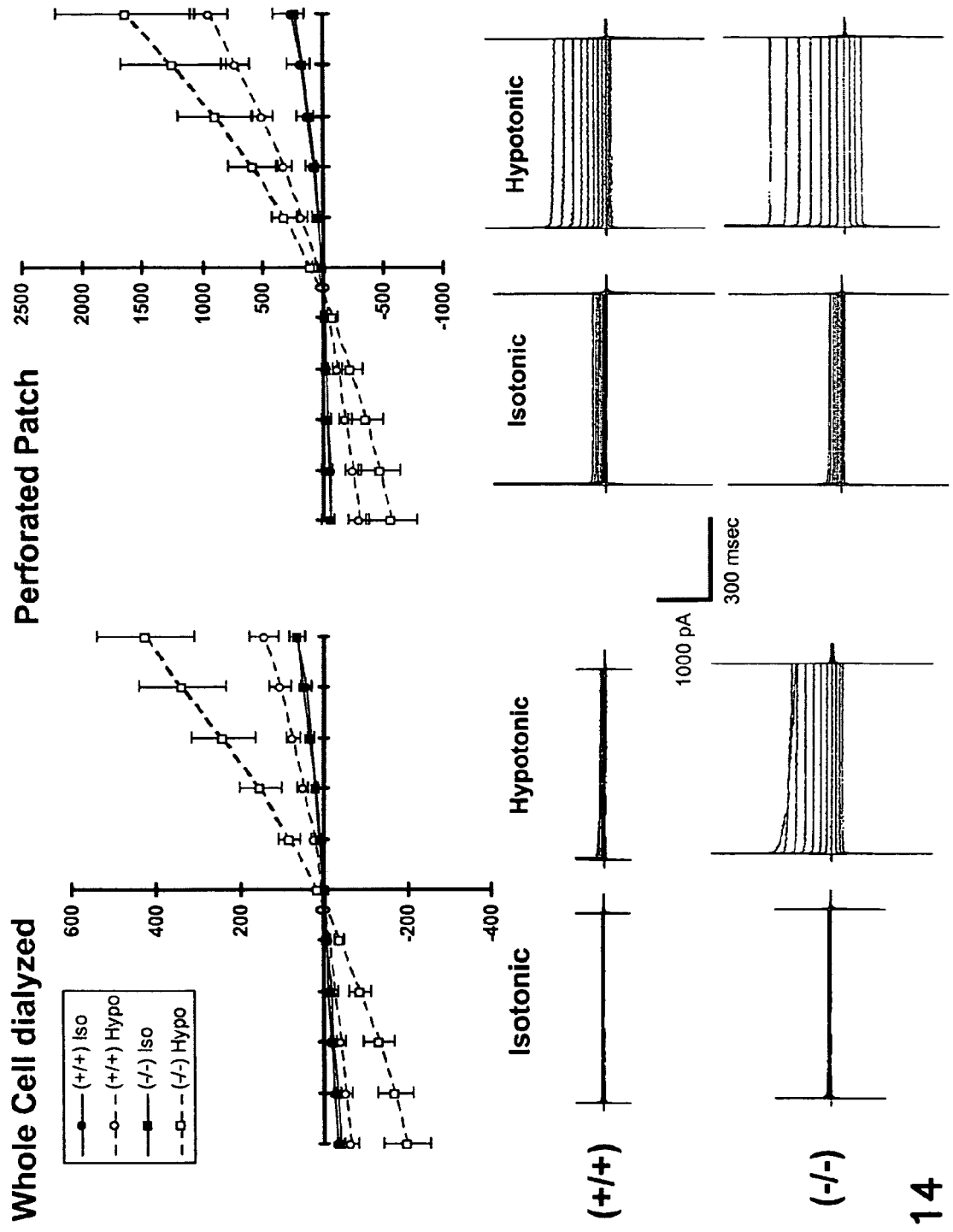
FIG. 14 shows ICl$_{swell}$ in cultured vascular smooth muscle cells. Left: Whole cell patch clamp recordings. Outward current is significantly larger in Clcn3$^{-/-}$ cells than in Clcn3$^{+/+}$ cells. Right: Perforated-patch recordings. A similar swelling-induced chloride current is present in both cell types. Note the lack of time-dependent inactivation under these recording conditions.

Baseline and swelling-induced Cl currents were measured in cultured vascular smooth muscle cells from both Clcn3$^{+/+}$ and Clcn3$^{-/-}$ cells (FIG. 14). In the dialyzed, whole-cell recording configuration, basal ICl was not different in the two sets of cells. The Clcn3$^{-/-}$ cells (membrane capacitance, 5.9±1.8 pF, n=5) underwent a significantly larger increase in ICl in response to a 50 mM decrease in extracellular osmolality (305–255 mOsm/Kg) than did Clcn3$^{+/+}$ cells (7.5±1.5 pF, n=5). The currents observed in both groups were typical of the well-characterized ICl$_{swell}$ seen in many cell types (Nilius et al., 1997). They were outwardly rectifying and showed inactivation at positive voltages (+80,+100 mV).

Perforated patch recording allows measurement of whole cell currents without the general disruption of the cytoplasmic environment that occurs during ruptured patch recording (Horn and Marty, 1988). The pore-forming antibiotic amphotericin was used to form monovalent ion-selective channels in the membrane patch. Under these conditions, only monovalent cations, water, and to a lesser extent chloride can move between the pipette and the cytosol. When the response to swelling was measured using this technique an increase in outwardly rectifying current was observed. The magnitude of the increase in current was not statistically different between Clcn3$^{+/+}$ (7.4±1.9 pF, n=5) and Clcn3$^{-/-}$ (6.9±1.2 pF, n=7) cells. Of note, when these non-dialyzed cells were exposed to osmotic stress, the resulting Cl current was outwardly rectifying but never displayed inactivation at positive voltages as is seen when ICl$_{swell}$ is measured in the whole-cell configuration. The reason for the absence of time-dependent inactivation under these conditions is not clear. It is possible that the inactivation process is related to the loss of some cytoplasmic factor that is associated with dialyzed whole-cell recording. Alternatively, the HEPES buffer that is commonly used in patch pipette solutions may be acting as an anion channel blocker and inhibiting outward current in a time-dependent fashion at very positive intracellular potentials (Hanrahan and Tabcharani, 1990). These data demonstrate that the ClC-3 protein cannot by itself account for the swelling-induced Cl current. The possibility that ClC-3 is one of a group of proteins responsible for this conductance cannot be ruled out.

Figure 15:
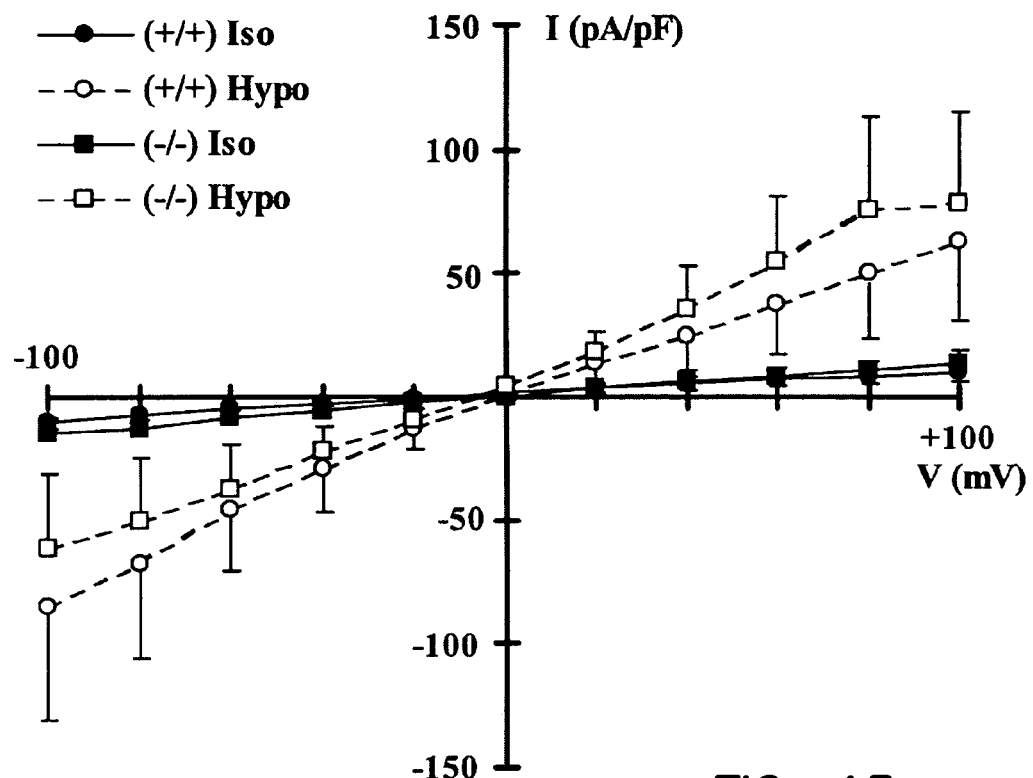
FIG. 15 shows ICl$_{swell}$ in cultured ES cells. There is no difference in the magnitude of inward or outward current induced by osmotic stress in Clcn3$^{-/-}$ and Clcn3$^{+/+}$ cells.

Cultured Clcn3$^{+/+}$ (2.1±0.2 pF, n=6) and Clcn3$^{-/-}$ (2.9±0.5 pF, n=6) ES cells undergo a similar average increase in current under hypotonic conditions (FIG. 15). However, even in Clcn3$^{+/+}$ cells, these currents generally were not typical of the ICl$_{swell}$ observed in either our vascular smooth muscle cells or in the literature (Nilius et al., 1997). Only a single Clcn3$^{-/-}$ cell had current that rectified outwardly and inactivated at positive potentials. Some currents were nearly linear and others showed some degree of inward rectification. The absence of a characteristic ICl$_{swell}$ in cells that clearly express Clcn3 message by PCR (FIG. 4E) provides further evidence of a dissociation between Clcn3 and this nearly ubiquitous ion current.

Human Genetic Analysis

No etiologic sequence variations were observed in this study. Two synonymous codon changes were observed. The first Ile770Ile (ATT→ATC) was observed in 16 control subjects (heterozygously in 15 individuals and homozygous in one individual). This change was also seen heterozygously in 12 patients with retinitis pigmentosa and in 16 patients with LCA. The second change, Thr807Thr (ACG→ACA), was noted in one normal control. Thus, based on the screening of 81 LCA and 92 RP patients, no evidence has been found for a mutation in this gene being associated with photoreceptor degeneration in humans.

Discussion

To directly test the cellular and in vivo functions of ClC-3 channels, we created a cell line and mice that lacked the Clcn3 gene. Some of these data have been reported in preliminary form (Schutte et al., 2000). Our Clcn3$^{-/-}$ knockout mice display kyphosis, priapism, absence of normal escape extension behavior, a high incidence of unexplained sudden death without obvious prodrome, and as we report elsewhere, altered vascular reactivity (Dickerson et al., 2001). There is no loss of the swelling-induced chloride current in cultured vascular smooth muscle cells that lack the Clcn3 gene. Although a typical ICl$_{swell}$ is not seen in either Clcn3$^{+/+}$ or Clcn3$^{-/-}$ ES cells, there is no difference in the magnitude of outward current activated by osmotic stress. We describe a central nervous system phenotype of the Clcn3$^{-/-}$ mouse that is similar in many, but not all, respects to that observed in a different, independently-produced line of Clcn3$^{-/-}$ mice (Stobrawa et al., 2001): postnatal loss of hippocampal neurons and degeneration of retinal photoreceptors accompanied by electroretinograms consistent with blindness. Despite the observation of spontaneous seizures in the knockout line, Clcn3$^{-/-}$ mice (4-5 weeks old) exhibit a marked and unexpected resistance to pentylenetetrazole-induced seizures compared to age-matched controls.

As presented in the introduction, there is significant controversy regarding the biophysical characteristics of the chloride current encoded by Clcn3. We tested the hypothesis that if Clcn3 encodes $ICl_{swell}$, that current should be lacking in $Clcn3^{-/-}$ cells. $Clcn_3^{-/-}$ vascular smooth muscle cells display a robust $ICl_{swell}$ which was either not different from that seen in $Clcn3^{+/+}$ cells (perforated patch recording), or under some conditions (dialyzed whole cell recording), was actually significantly larger. These results suggest that, if ClC-3 contributes to $ICl_{swell}$, it is not the only channel involved. It is possible that the loss of ClC-3 channels leads to up-regulation of other chloride channel proteins that also contribute to the current. Prime candidates for this role might be ClC-4 or ClC-5 whose structures are highly related to that of ClC-3. $ICl_{swell}$ could also involve heterodimeric proteins combining different members of the ClC family. Previous work did not reveal up-regulation of ClC-4 or ClC-5 expression in the brain of $Clcn3^{-/-}$ mice (Stobrawa et al., 2001).

The outward currents induced by hypotonic stress in $Clcn3^{+/+}$ and $Clcn3^{-/-}$ ES cells did not resemble a typical $ICl_{swell}$ with outward rectification and voltage-dependent inactivation. These currents were highly variable and could include contributions from both anion channels and non-selective cation channels. The absence of an $ICl_{swell}$ in ES cells is not due to lack of Clcn3 message (FIG. 1E). Although it is possible that message is present and no protein is made, this observation further supports the contention that Clcn3 is unlikely to encode $ICl_{swell}$.

The $Clcn3^{-/-}$ mouse's constellation of kyphosis, waddling gait, and rear-leg folding behavior upon suspension by the tail, resemble the triad of features displayed by a mouse model of Duchenne muscular dystrophy (Orita et al., 1989). This led us to hypothesize that these features of the $Clcn3^{-/-}$ mouse were secondary to muscular weakness. We detected no clear difference in forelimb grip strength between $Clcn3^{+/-}$ and $Clcn3^{-/-}$ mice (data not shown) and observed no light-microscopic evidence of skeletal muscle myopathy in $Clcn3^{-/-}$ mice. We also found that creatine kinase levels were not elevated in either young adult or older adult $Clcn3^{-/-}$ mice, suggesting that if a myopathy were indeed present, it does not involve a rapid degeneration of myocytes. Although these findings do not support a primary abnormality of muscle function, we cannot rule out an ultrastructural abnormality that might only be detectable by electron microscopy. ClC-3 protein expression has not been confirmed in skeletal muscle but ClC-3 message has been detected by Northern analysis in both human and mouse tissues (Borsani et al., 1995).

Absence of escape extension with rear leg folding is also observed in 'tauopathy' (Lewis et al., 2000) in a transgenic mouse line expressing mutant human (P301L) tau, a protein implicated in Alzheimer disease and other CNS disorders. Neurofibrillary tangles, amyotrophy and progressive motor disturbances are observed in these mice. The severity, spectrum of symptoms, and rapid progression of pathology in tauopathy are quite different from the features observed in our $Clcn^{-/-}$ mice. However, the similarity of the abnormal hindlimb response (at least in early stages of tau mice pathology) may implicate neurological mechanisms in the observation of lack of escape extension in $Clcn^{-/-}$ mice.

There is evidence that absence of escape extension, kyphosis, and priapism can result from neurological abnormalities. For example, the constellation of locomotor instability, quivering, varying degrees of hindlimb weakness, clasping of the hindlimbs when held by the tail, and priapism in males is observed in the quivering mouse (qv) (Yoon, 1960 and Yoon et al., 1957). These animals have histologically normal brains, spinal cords and nerve roots although they do have deafness of central origin (Bock et al., 1983). However, an allelic variant of the qv mouse, $qv^{lnd}$ (lumbosacral neuraxonal degeneration) has dystrophic neurons in the low lumbar and sacral spinal cord. The qv locus is located on mouse chromosome 7 while Clcn3 maps to chromosome 8 (Mills et al., 1995). The combination of growth failure, thoracolumbar kyphosis and priapism is also seen in the $Ggtp^{enul}$ mouse (Harding et al., 1997) lacking γ-glutamyl transpeptidase activity. This mutation results in glutathionuria and cysteine deficiency. No specific neurologic abnormality has been defined. The only other previously described murine model of priapism is the Priap 1 mouse (Adams et al., 2001). These animals are exceptionally long lived and senile weight loss is associated with the onset of priapism. It was speculated that the mechanism of the priapism was related to undefined neurologic abnormalities.

Priapism also could result from a primary abnormality in neurovascular function. We describe elsewhere a diminished postsynaptic contractile response to norepinephrine in aortic vascular smooth muscle from male $Clcn3^{-/-}$ mice (Dickerson et al., 2001). Clinical priapism in humans can result from the use of alpha-adrenergic antagonists such as phentolamine and can be treated with local application of alpha-adrenergic agonists (Lue et al., 1986). $Clcn3^{-/-}$ mice may also have altered presynaptic function of sympathetic nerve endings. Abnormalities in synaptic vesicular acidification have been described in the $Clcn3^{-/-}$ mouse (Stobrawa et al., 2001). Loss of a vesicular chloride channel interferes with charge neutralization across the vesicular membrane and thereby limits the magnitude of the proton gradient that can be created by the vesicular $H^+$-ATPase. Synaptosomal monoamine uptake involves the exchange of two luminal protons for one cytoplasmic monoamine (Knoth et al., 1981). The lack of a synaptosomal chloride conductance could theoretically lead to reduced norepinephrine uptake into, and release from, sympathetic synaptic vesicles in the $Clcn3^{-/-}$ mouse. We hypothesize that a combination of diminished norepinephrine release and reduced smooth muscle contractility could lead to an inability to properly regulate blood flow into the corpus cavernosum and result in priapism.

ClC-3 is expressed in renal collecting duct type B intercalated cells (Obermuller et al., 1998) and conceivably could contribute to acid-base abnormalities. Virtually nothing is known about the function of ClC-3 in renal physiology. We detected no abnormalities in serum osmolality, electrolytes, acid-base regulation, or creatininc clearance. However, a more detailed examination of renal function, particularly after challenges to pH regulation might have revealed abnormalities.

The severe retinal degeneration demonstrated both by non-detectable ERG signals in vivo and by retinal histology suggested that this gene was a good candidate for inherited photoreceptor degenerations in humans. Genes responsible for other mouse models of photoreceptor degeneration subsequently have been shown to be mutated in human photoreceptor degenerations (Gal et al., 2000). One of the most severe early onset photoreceptor degenerations in humans is LCA. This term refers to a group of inherited retinal disorders characterized by severe, bilateral visual impairment in infancy. The ERG responses are markedly attenuated from birth. Systemic disorders, most often neurological, are observed in a small number of individuals. To date, mutations in seven genes have been reported to cause a subset of LCA (Perrault et al., 1996; Marlhens et al., 1997; Gu et al., 1997;

Freund et al., 1998; Lewis et al., 1999; Sohocki et al., 2000; Lotery et al., 2001; Dryja, 2001 #901). However, mutations in these genes still only account for a small percentage of LCA cases (Gal et al., 2000). The combination of both neurological and retinal abnormalities seen in Clcn3$^{-/-}$ mice suggested that an additional fraction of LCA cases may be caused by mutation in the CLCN3 gene.

RP is a term used to refer to another clinically and genetically heterogeneous group of retinal degenerations that are closely related to LCA. In fact, the distinction between LCA and RP is largely based on age of onset of visual dysfunction. The similarity of these conditions suggests that genes known to cause RP might also cause some cases of LCA. Indeed, four of the known LCA-associated genes (RPE65, CRX, TULP, CRB1) are each known to cause some cases of RP (Sohocki et al., 2000; Morimura, 1998 #911, Banerjee, 1998 #912, Hagstrom, 1998 #913). We therefore also screened a cohort of RP patients for mutations in the Clcn gene.

We found no mutations in the coding region of the human CLCN3 gene in patients with either LCA or RP. Indeed, the allelic variation of this gene was much less than other genes we have studied (Webster et al., 2001) with only two synonymous coding variations noted. However, it is important to recognize that mutations not detected by our PCR-based assay of the coding region of this gene may still be present. These would include mutations in the promoter region of the gene or large deletions. In view of the Clcn3$^{-/-}$ mouse phenotype it would be useful to assess this gene for mutation in other human diseases that combine severe photoreceptor degeneration with neurological abnormalities.

In this study, we report several important new CNS-related findings with respect to hippocampal degeneration and altered neural function in Clcn3$^{-/-}$ mice. The hippocampal formation is one of the most epileptogenic regions of the rodent brain (Lothman, 1993 and Stringer, 1994) and lesions at any site within it can lower the threshold to seizures and induce epilepsy (Lothman, 1993 and Bonthius et al., 2001). Furthermore, the hippocampal formation is involved in the major motor seizures induced by PTZ (Stringer, 1994). These observations, combined with the finding that our mice undergo hippocampal neuronal loss prompted the hypothesis that the knockout mice would have a lowered threshold to PTZ-induced seizures. Surprisingly, Clcn3$^{-/-}$ mice (4-5 weeks old) exhibit a marked and unexpected resistance to pentylenetetrazole-induced seizures compared to age-matched controls. This resistance to PTZ-induced seizures may be due to interruption of the circuitry of the hippocampal formation by very early stages of degeneration (i.e. synaptic disruption) that is not yet evident under light microscopy. Thus, while individual neurons could be in a state of increased irritability, the network properties of the neural circuits would no longer be sufficient to support the ensemble excitation and re-excitation necessary for generation of limbic seizures.

We also observed that adult Clcn3$^{-/-}$ mice are extremely sensitive to, and exhibit a markedly prolonged recovery from, benzodiazepines and barbiturates. There is an increased incidence of death from pentobarbital. Resistance to PTZ, an inhibitor of GABA$_A$ receptors, combined with an increased sensitivity to sedative agents that enhance activity of GABA$_A$ receptors (pentobarbital and midazolam), may point to an abnormality in GABA neurotransmission. The effect of losing a synaptic vesicular chloride conductance on GABA uptake may be difficult to predict (Bosl et al., 2001 and Stobrawa, 2001). Unlike monoamine uptake, GABA uptake is dependent upon both the proton gradient and the electrical gradient across the vesicular membrane (Reimer et al., 1998). Loss of a vesicular chloride conductance is expected to decrease the proton gradient but increase the electrical gradient. Miniature inhibitory postsynaptic currents (GABAergic) were not altered in CA1 pyramidal cells from Clcn3$^{-/-}$ mice (Stobraw, 2001). It remains to be determined how the loss of ClC-3 channels affects GABAergic neurotransmission in a complex neural network.

Degeneration of the hippocampal formation in Clcn3$^{-/-}$ mice was reported previously (Stobrawa, 2001). Our study confirms and extends that finding by demonstrating that the time course of hippocampal cell loss depends on the anterior-posterior (septal-temporal) location of the cells. We found that neuronal cell loss occurs consistently and considerably earlier in the anterior portion of the hippocampus and dentate gyrus than in the posterior portion. Whether the ultimate severity of cell loss differs along the anterior-posterior axis is unclear. Certainly, neuronal loss in the anterior portion is complete, as no hippocampal neurons survive there. Neuronal loss in the posterior hippocampus is considerable by PD330, but a proportion of hippocampal neurons remain alive there. Whether all neurons ultimately would be lost from the posterior hippocampus remains unknown.

The sequential loss of hippocampal neuronal subpopulations, which began in the dentate gyrus, and progressed to involve CA3 followed by CA1 is a different sequence from that observed previously (Stobrawa, 2001). That report described degeneration of the same hippocampal neuronal populations, but in the opposite order and at a substantially faster rate, such that virtually complete degeneration of the hippocampal formation occurred by PD42. This disparity in both sequence and rate of neuronal loss is puzzling, particularly as the time course of retinal degeneration appears to be very similar in these independently derived Clcn3$^{-/-}$ populations.

We find that the progression of neuronal dropout between regions of the hippocampus follows the principal circuitry of the hippocampal formation. The dentate gyrus is the major recipient of extra-hippocampal afferent input. The dentate gyrus projects mossy fibers to CA3 pyramidal cells, which project to CA1 pyramidal cells via Shaffer collaterals (Bayer, 1985). This unidirectional dentate gyrus to CA3 to CA1 projection is termed the "trisynaptic circuit" (Witter et al. 2000). The matching of ordered neuronal dropout to this connectional anatomy suggests that transynaptic degeneration may underlie some of the neuronal loss in Clcn3$^{-/-}$ mice (Chang, 1998 and Yamada et al., 1994).

Although the intrinsic circuitry of the hippocampal formation is quite uniform throughout its septo-temporal extent, important differences in its afferent and efferent connections exist along its longitudinal axis (Witter et al., 2000 and Witter, 1986). The major inputs to posterior hippocampus are derived from the medial entorhinal cortex, amygdala and interpeduncular nuclei. In contrast, chief sources of afferent input to the anterior hippocampus arise from lateral entorhinal cortex, perirhinal cortex and raphe nuclei. Differences in time course of neurodegeneration between the anterior and posterior portions of the hippocampus may be related to these differences in circuitry.

Hippocampal neuronal cell loss is accompanied by substantial astrogliosis. In addition, microgliosis has been documented previously within the same region (Stobrawa, 2001). The presence of astrogliosis is relevant to the utility of the Clcn3$^{-/-}$ mouse as a model for human hippocampal sclerosis. Hippocampal sclerosis is a major cause of temporal lobe epilepsy in humans and is defined not only by the loss of hippocampal neurons, but also by the replacement of hippocampal neurons by astrocytes (Van Paesschen et al., 1997). The cause of hippocampal sclerosis is unknown, but genetic factors may play a role (Berkovic et al., 2000). The findings of this study raise the intriguing possibility that hippocampal sclerosis in some patients may be caused by a genetic defect in chloride conductance.

Mice lacking the Clcn3 gene exhibit complex phenotypic abnormalities that are not limited to the CNS (e.g., kyphosis, priapism), but that could still be related to alterations in neuronal function. These abnormalities cannot be accounted for by an absence of the swelling-activated chloride conductance, because $ICl_{swell}$ is still present.

Example 7

Dose-response Curves to Norepinephrine in Isolated Aortic Rings from Male Wild-type (+/+), Heterozygote (+/−) and Clcn3 Knockout (−/−) Mice.

Methods

Animals were sacrificed by exposure to 100% $CO_2$ for five minutes followed by cervical dislocation. Thoracic aortae were removed, cleaned of adherent connective tissue and cut into 4 rings. The endothelium was left intact and the rings were mounted in a Multi Myograph Model 610M (Danish Myotechnology A/S, Aarhus, Denmark). Contractile responses were recorded using a MacLab 8E and stored on a Power MacIntosh 6400/200 computer. Passive stretch was set at 5.0 mN and the rings were allowed to equilibrate in Physiologic Salt Solution (PSS) at 37° C. for 60 minutes prior to the start of experimentation. PSS was aerated with a mixture of 95% $O_2$ and 5% $CO_2$; the composition was as follows (mM): NaCl 119, KCl 4.7, $KH_2PO_4$ 1.18, $MgSO_4.7H_2O$ 1.17, $NaHCO_3$ 25, $CaCl_2.2H_2O$ 2.5, dextrose 5.5, $CaNa_2$ EDTA 0.027, pH was 7.30.

Results

Figure 16:
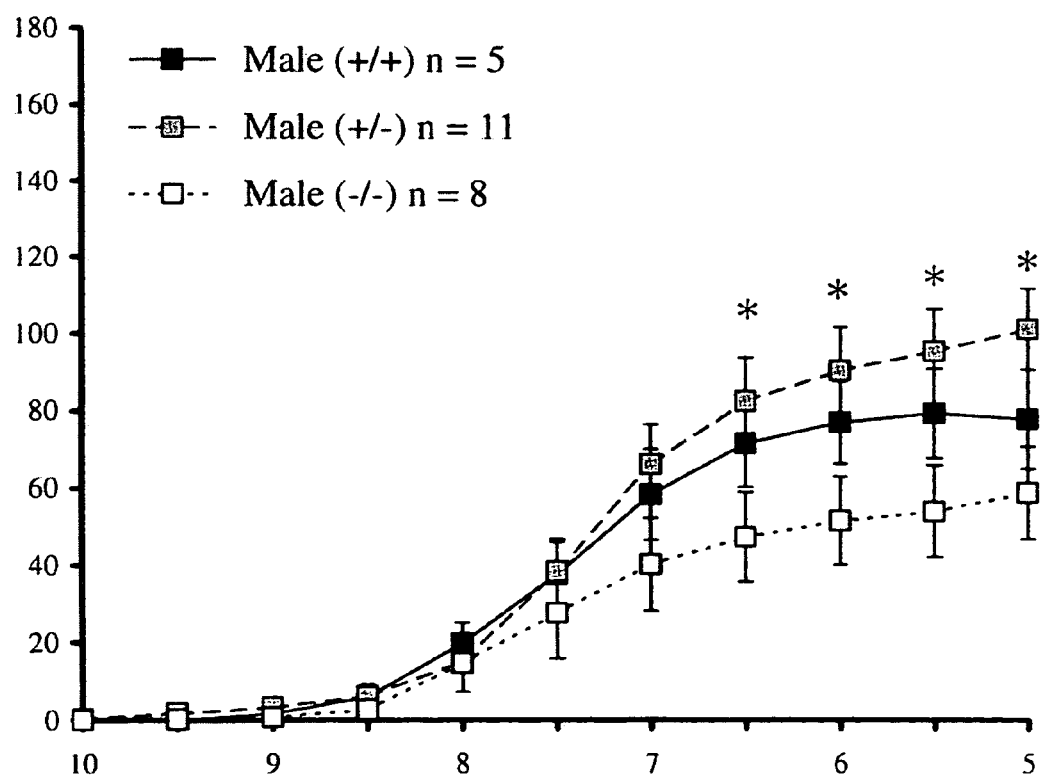
FIG. 16 shows dose-response to norepinephrine under control conditions.
Figure 17:
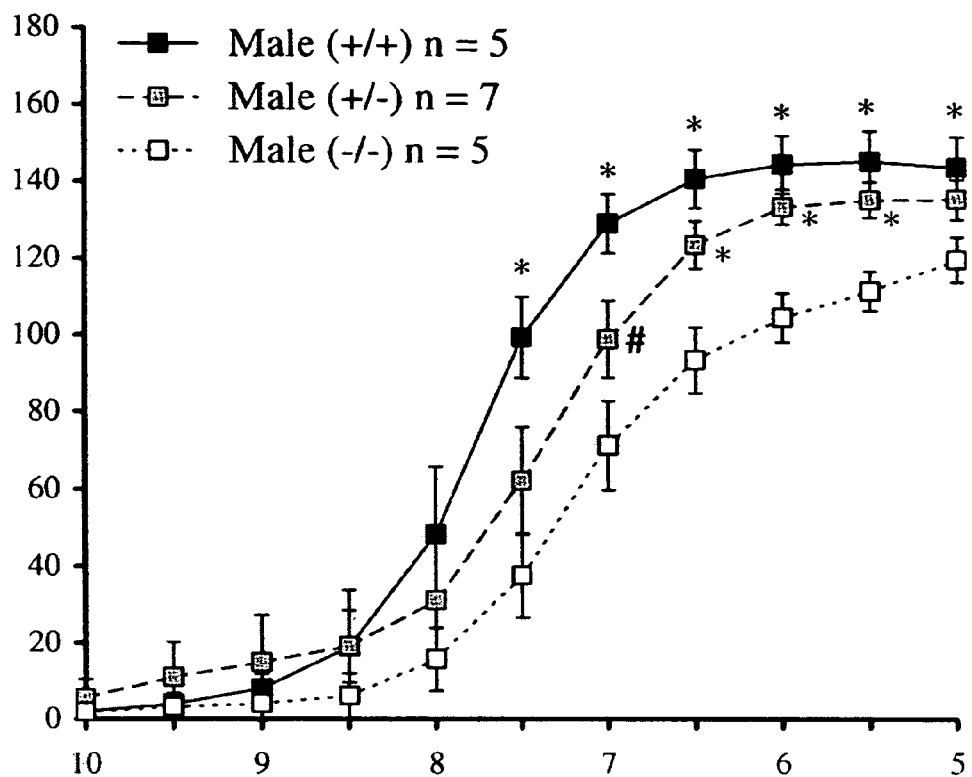
FIG. 17 shows dose-response to norepinephrine in the presence of L-NNA ($10^{-4}$ M).
Figure 18:
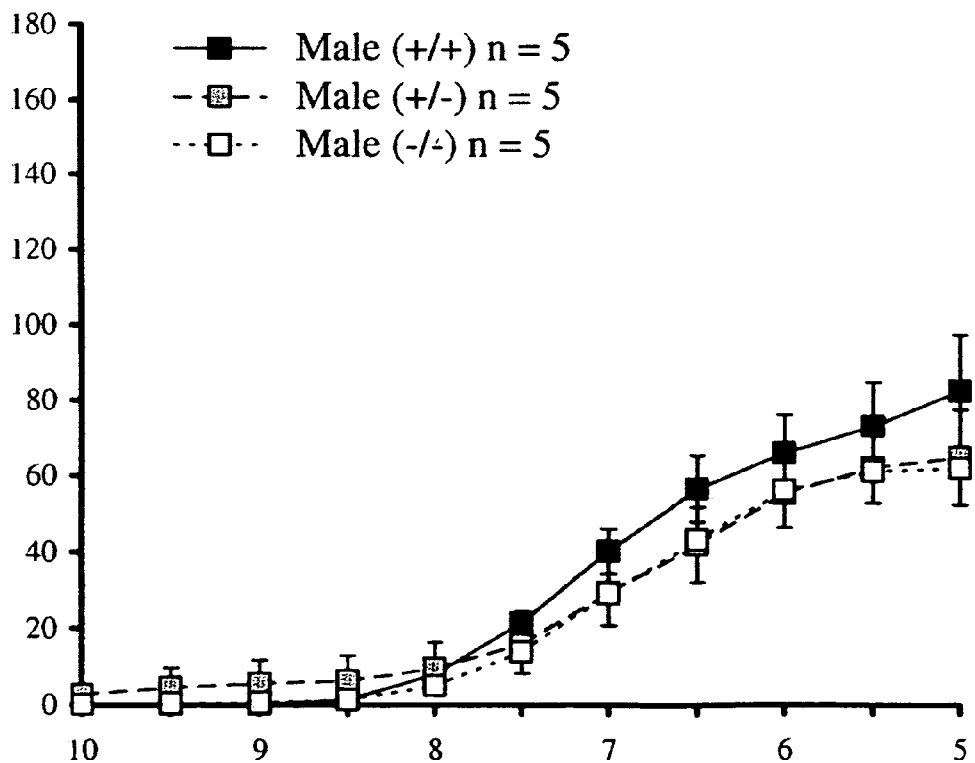
FIG. 18 shows dose-response to norepinephrine in the presence of L-NNA ($10^{-4}$ M) and nifedipine ($10^{-6}$ M).

The data are obtained under three different conditions: 1) control, 2) L-NNA-treated (10-4 M), and 3) L-NNA+nifedipine-treated. There is a small difference between knockout and wild-type responses and a significant difference between knockout and heterozygote responses under control conditions (FIG. 16). When endothelial nitric oxide synthase is inhibited, the normal increase in responsiveness, as seen in the wild-type tissues is diminished in the heterozygote and even further diminished in the knockout tissues (FIG. 17). When nifedipine is added in addition to L-NNA and used to block voltage-sensitive calcium channels (FIG. 18), the tissues are all much less reactive to norepinephrine as would be expected. Under these conditions the difference in reactivity to norepinephrine is removed. This suggests that the cause of the diminished contractile responsiveness to norepinephrine in the Clcn3 knockout tissues is a failure to normally activate voltage-sensitive calcium channels. Asterisks indicate a significant difference in contractile responses between groups ($p<0.05$).

These results are consistent with the hypothesis that ClC-3 chloride channels are under the tonic, inhibitory influence of endothelial nitric oxide. Norepinephrine activates the channels more efficiently in the absence of nitric oxide. This results in more depolarization, more activation of voltage-sensitive calcium channels, and larger contractile responses. The knockout animal is not subject to the same degree of potentiation of contraction by L-NNA because ClC-3 is lacking. These data are consistent with earlier data showing that ClC-3 channel inhibitors were much more effective vasodilators of isolated rat aortic tissue when endothelial function was disrupted.

All publications, patents and patent documents are incorporated by reference herein, as though individually incorporated by reference. The invention has been described with reference to various specific and preferred embodiments and techniques. However, it should be understood that many variations and modifications may be made while remaining within the scope of the invention.

REFERENCES

Adams D. D. et al., *Mech. Ageing Dev.*, 122, 173-189 (2001).
Bayer S A., *The Rat Nervous System*, Vol. 1, Forebrain and Midbrain, 335-352, (1985).
Berkovic S. F. et al., *Ann. Neurol.*, 47, 557-558 (2000).
Bock G. R. et al., *Acta Otolarvngol.*, 96, 371-377 (1983).
Bonthius D. J. et al., *Alcohol Clin. Exp. Res.*, 25, 70-82 (2001).
Borsani G. et al., *Genomics*, 27, 131-141 (1995).
Bosl M. R. et al., *Embo J.*, 20, 1289-1299 (2001).
Buffone G. J. et al., *Clin. Chem.*, 31, 164-165 (1985).
Chang C. W., *Electroencephalogr. Clin. Neurophysiol.*, 109, 199-202 (1998).
Dickerson L. W. et al., *FASEB J.*, 15, A114 (2001).
Duan D. et al., *J. Gen. Physiol.*, 113, 57-70 (1999).
Duan D. et al., *J. Physiol. (Lond.)*, 531 Pt. 2, 437-44 (2001).
Duan D. et al., *Nature*, 390, 417-421 (1997).
Fahlke C. et al., *J. Gen. Physiol*, 109, 93-104 (1997).
Freshney R I. *Culture of Animal Cells: A Manual of Basic Technique*. New York: Wiley-Liss/John Wiley & Sons, Inc., 2000.
Kieferle S. et al., *Proc. Natl. Acad. Sci. USA*, 91, 6943-6947 (1994).
Freund C. L. et al., *Nat. Genet.*, 18, 311-312 (1998).
Friedrich T. et al., *J. Biol. Chem.* 274, 896-902 (1999).
Gal A. et al., *Nat. Genet.* 26, 270-271 (2000).
Gu S. M. et al., *Nat. Genet.*, 17, 194-197 (1997).
Hamill O. P. et al., *Pflugers Arch.*, 391, 85-100 (1981).
Hanrahan J. W. et al., *J. Membr. Biol.*, 116, 65-77 (1990).
Harding C. O. et al., *J. Biol. Chem.*, 272, 12560-12567 (1997).
Horn R. et al., *J. Gen. Physiol.*, 92, 145-159 (1988).
Huang P. et al., *J. Biol. Chem.*, JBC online accepted manuscript (2001).
Jentsch T. J. et al., *Pflugers Arch*, 437, 783-795 (1999).
Kawasaki M. et al., *Neuron*, 12, 597-604 (1994).
Klocke R. et al., *J. Biol. Chem.*, 269, 27635-27639 (1994).
Knoth J. et al., *Biochemistry*, 20, 6625-6629 (1981).
Koch M. C. et al., *Science*, 257, 797-800 (1992).
Komak U. et al., *Cell*, 104, 205-215 (2001).
Lewis C. A. et al., *Invest. Ophthalmol. Vis. Sci.*, 40, 2106-2114 (1999).
Lewis J. et al., *Nat. Genet.*, 25, 402-405 (2000).
Li X. et al., *J. Biol. Chem.*, 275, 35994-35998 (2000).
Lloyd S. E. et al., *Nature*, 379, 445-449 (1996).
Loscher W. et al., *Epilepsy Res.*, 9, 1-10 (1991).
Lotery A. J. et al., *Arch. Ophthalmol.*, 119, 415-420 (2001).
Lothman E. W., *Pediatric Epilepsy: Diagnosis and Therapy*, 1-15 (1993).
Ludewig U. et al., *Nature*, 383, 340-343 (1996).
Lue T. F. et al., *J. Urol.*, 136, 104-108 (1986).
Marlhens F. et al., *Nat. Genet.*, 17, 139-141 (1997).
Mills K. A. et al., *Mammalian Genome*, 6, 278-280 (1995).
Miyazaki H. et al., *Biochem. Biophys. Res. Commun.*, 255, 175-181 (1999).
Nilius B. et al., *Prog. Biophys. Mol. Biol.*, 68, 69-119 (1997).
Obermuller N. et al., *J. Clin. Invest.*, 101, 635-642 (1998).
Oguro K. et al., *J. Neurosci.*, 19, 9218-9227 (1999).
Orita M. et al, *Proc. Natl. Acad. Sci. USA*, 86, 2766-2770 (1989).

Palmer S. et al., *Nat. Genet.*, 10, 472-476 (1995).
Perrault I. et al., *Nat. Genet.*, 14, 461-464 (1996).
Piwon N. et al., *Nature*, 408, 369-373 (2000).
Reimer R. J. et al., *Curr. Opin. Neurobiol.*, 8, 405-412 (1998).
Schutte B. C. et al., *FASEB J.*, 14, A54 (2000).
Schwappach B. et al., *J. Biol. Chem.*, 273, 15110-15118 (1998).
Sheffield V. C. et al., *Genomics* 16, 325-332 (1993).
Shimada K. et al., *Am. J. Physiol. Gastrointest. Liver. Physiol.*, 279, G268-276 (2000).
Simon D. B. et al., *Nature Genetics*, 17, 171-178 (1997).
Sohocki M. M. et al., *Mol. Genet. Metab.*, 70, 142-150 (2000).
Sohocki M. M. et al., *Nat. Genet.*, 24, 79-83 (2000).
Squires R. F. et al., *Life Sci*, 35, 1439-1444 (1984).
Stobrawa S. M., *Neuron*, 29, 185-196 (2001).
Stringer J. L. *Brain Res.*, 636, 221-226 (1994).
Thevenod F. et al., *FASEB J.* 14, A109 (2000); (Thevenod et al. II).
Thevenod F. et al., *J. Korean Med. Sci.*, 15, S51-52 (2000); (Thevenod et al. I).
Uchida S. et al., [In Process Citation] *Exp. Nephrol.*, 8, 361-365 (2000).
Uchida S. et al., *Nephrol Dial Transplant*, 15, 14-15 (2000).
Van Paesschen W. et al., *Ann. Neurol*, 42, 756-766 (1997).
Waldegger S. et al., *J. Biol. Chem.*, 275, 24527-24533 (2000).
Wang L. et al., *J. Physiol. (Lond.)*, 524 Pt. 1, 63-75 (2000).
Webster A. R. et al., *Invest. Ophthalmol. Vis. Sci.*, 42, 1179-1189 (2001).
Weylandt K. H. et al., *J. Biol. Chem.*, 276, 17461-174617 (2001).
Wiley-Liss/John Wiley & Sons Inc. (2000).
Witter M. P. et al., *Ann. N Y Acad. Sci.*, 911, 1-24 (2000).
Witter M. P., *Adv. Exp. Med. Biol.*, 203, 67-82 (1986).
Yamada K. et al., *Neuroscience*, 62, 793-801 (1994).
Yoon C. H. et al., *J. Hered.*, 48, 176-180 (1957).
Yoon C. H., *Am. Naturalist*, 94, 435-440 (1960).

What is claimed is:

1. A method to modulate vascular tone in a male patient having compromised vascular tissue associated with erectile dysfunction, comprising administering to the male patient a pharmaceutically effective amount of a chloride channel blocking agent, or a pharmaceutically acceptable salt thereof.

2. A method of claim 1, wherein the chloride channel blocking agent is a compound of Formula I

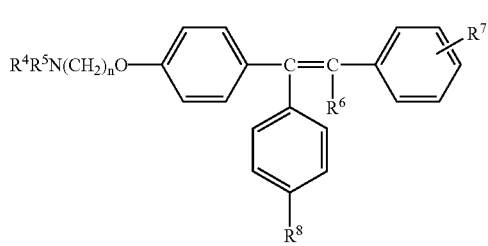

wherein either $R^4$ is H or a lower alkyl radical and $R^5$ is a lower alkyl radical, or $R^4$ and $R^5$ are joined together with the adjacent nitrogen atom to form a heterocyclic radical;

$R^6$ is H or a lower alkyl radical;

$R^7$ is H, halo, OH, a lower alkyl radical, or is a buta-1,3-dienyl radical which together with the adjacent benzene ring forms a naphthyl radical;

$R^8$ is H or OH; and n is 2;

or a pharmaceutically acceptable salt thereof.

3. A method of claim 2, wherein the compound is 1-p-β-dimethylaminoethoxyphenyl-trans-1,2-diphenylbut-1-ene, or a pharmaceutically acceptable salt thereof.

4. A method of claim 1, wherein the chloride channel is a CLC3 channel.

5. The method of claim 4, wherein blocking the CLC3 channel results in diminished vasoconstriction to norepinephrine.

6. The method of claim 1, wherein the agent modulates vascular tone by enhancing vasodilation.

7. A method of claim 1, further comprising administering a pharmaceutically effective compound selected from an anti-diabetes agent, an anti-hypertension agent, an anti-coronary artery disease agent, an anti-restenosis agent, and a vasodilatory agent.

8. A method of claim 1, wherein the agent is administered intravenously or orally.

9. A method to modulate penile vascular tone in a male mammal in need thereof, said method comprising administering a pharmaceutically effective amount of a chloride channel blocking agent, or a pharmaceutically acceptable salt thereof.

10. A method of claim 9, wherein the chloride channel blocking agent is a compound of Formula I

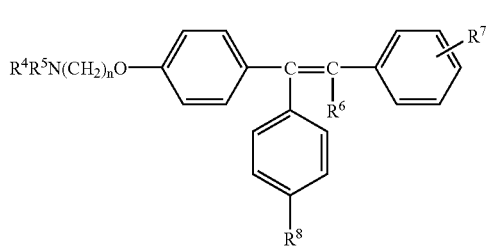

wherein either $R^4$ is H or a lower alkyl radical and $R^5$ is a lower alkyl radical, or $R^4$ and $R^5$ are joined together with the adjacent nitrogen atom to form a heterocyclic radical;

$R^6$ is H or a lower alkyl radical;

$R^7$ is H, halo, OH, a lower alkyl radical, or is a buta-1,3-dienyl radical which together with the adjacent benzene ring forms a naphthyl radical;

$R^8$ is H or OH; and n is 2;

or a pharmaceutically acceptable salt thereof.

11. A method of claim 10, wherein the compound administered is 1-p-β-dimethylaminoethoxyphenyl-trans-1,2-diphenylbut-1-ene, or a pharmaceutically acceptable salt thereof.

12. The method of claim 9, wherein the agent is administered orally or intravenously.

13. A method of claim 9, wherein the chloride channel is a CLC3 channel.

14. The method of claim 13, wherein blocking the CLC3 channel results in diminished vasoconstriction to norepinephrine.

15. The method of claim 13, wherein blocking the CLC3 channel reduces penile sympathetic tone.

16. The method of claim 15, wherein the reduction of penile sympathetic tone induces an erection.

17. A method for treating erectile dysfunction in a male patient comprising administering to the male patient a composition comprising a CLC3 channel blocking agent or a pharmaceutically acceptable salt thereof, and a pharmaceutically acceptable carrier.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tacatgttgc ctgctgctgt                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctgcagcact caactccaga                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgaatgaact gcaggacgag                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
```

```
atactttctc ggcaggagca                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agtggaaaac atgggcagag                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acggctgtta ccaaatggat                                              20

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gggcctcgag gaatgtgtgt cagttagggt gtgg                              34

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggccgattaa ttaatgcagc tggcacgaca gg                                32
```